(12) United States Patent
Grossman et al.

(10) Patent No.: US 10,456,493 B2
(45) Date of Patent: Oct. 29, 2019

(54) INFECTION CONTROL APPARATUS

(71) Applicant: Allied Bioscience, Inc., Plano, TX (US)

(72) Inventors: Craig Grossman, Point Roberts, WA (US); Ingrida Grossman, Point Roberts, WA (US); Gavri Grossman, Point Roberts, WA (US)

(73) Assignee: Allied Bioscience, Inc., Dallas, TX (US)

( * ) Notice: Subject to any disclaimer, the term of this patent is extended or adjusted under 35 U.S.C. 154(b) by 0 days.

(21) Appl. No.: 16/013,185

(22) Filed: Jun. 20, 2018

(65) Prior Publication Data

US 2018/0369438 A1    Dec. 27, 2018

Related U.S. Application Data

(60) Provisional application No. 62/524,320, filed on Jun. 23, 2017, provisional application No. 62/524,313, filed on Jun. 23, 2017.

(51) Int. Cl.
*C12Q 1/04* (2006.01)
*A61L 2/24* (2006.01)
(Continued)

(52) U.S. Cl.
CPC ............... *A61L 2/24* (2013.01); *A61L 2/18* (2013.01); *A61L 2/22* (2013.01); *C12Q 1/04* (2013.01); *C12Q 1/06* (2013.01); *C12Q 1/6869* (2013.01); *C12Q 1/6888* (2013.01); *G06K 7/10475* (2013.01); *G06K 7/1413* (2013.01); *G06K 19/06028* (2013.01); *G06K 19/07758* (2013.01);
(Continued)

(58) Field of Classification Search
CPC .... A61L 2/24; A61L 2/18; C12Q 1/04; C12Q 1/06; C12Q 1/6869; C12Q 1/6888; G06K 7/10475; G06K 7/1413; G06K 19/06028; G06K 19/07758
See application file for complete search history.

(56) References Cited

U.S. PATENT DOCUMENTS 6,017,561 A    1/2000  Zhou et al.
6,080,387 A    6/2000  Zhou et al.
(Continued)

FOREIGN PATENT DOCUMENTS

WO    2014049370    4/2014
WO    2014089559    6/2014
(Continued)

OTHER PUBLICATIONS

U.S. Appl. No. 15/938,417, filed Mar. 28, 2018.
(Continued)

*Primary Examiner* — Sean E Conley
(74) *Attorney, Agent, or Firm* — Snell & Wilmer L.L.P.

(57) ABSTRACT

An apparatus is provided for controlling hospital acquired infections by targeting critical control points for pathogen transfer. An infection control apparatus comprises an asset tagging unit; a spraying unit; a power supply unit; optionally a DNA/RNA sequencing unit; and a computing unit comprising a non-transitory computer-readable medium encoded with program instructions for controlling the asset tagging unit and the spraying unit to perform a method of infection control in the facility. In general, the apparatus is used to identify which assets are critical control points for pathogen transfer and to treat those assets with a residual self-sanitizing coating.

19 Claims, 8 Drawing Sheets

(51) Int. Cl.
  *C12Q 1/06*     (2006.01)
  *C12Q 1/6869*   (2018.01)
  *A61L 2/18*     (2006.01)
  *G06K 19/06*    (2006.01)
  *G06K 7/10*     (2006.01)
  *G06K 7/14*     (2006.01)
  *G06K 19/077*   (2006.01)
  *C12Q 1/6888*   (2018.01)
  *A61L 2/22*     (2006.01)

(52) U.S. Cl.
  CPC ....... *A61L 2202/14* (2013.01); *A61L 2202/15* (2013.01); *A61L 2202/16* (2013.01); *A61L 2202/25* (2013.01)

(56) References Cited

U.S. PATENT DOCUMENTS

| | | |
|---|---|---|
| 6,270,754 B1 | 8/2001 | Zhou et al. |
| 6,482,392 B1 | 11/2002 | Zhou et al. |
| 9,107,973 B1 | 8/2015 | Robinson et al. |
| 9,528,009 B2 | 12/2016 | Grossman et al. |
| 9,757,769 B2 | 9/2017 | Grossman et al. |
| 9,855,584 B2 | 1/2018 | Grossman et al. |
| 9,856,360 B2 | 1/2018 | Moros et al. |
| 9,918,475 B2 | 3/2018 | Moros et al. |
| 9,963,596 B2 | 5/2018 | Moros et al. |
| 2010/0008921 A1 | 1/2010 | Pohlner et al. |
| 2012/0291667 A1 | 11/2012 | Geoffrion et al. |
| 2014/0167917 A2 | 6/2014 | Wallace et al. |
| 2015/0118107 A1 | 4/2015 | Sunkara et al. |
| 2015/0165459 A1 | 6/2015 | Venard et al. |
| 2015/0205985 A1 | 7/2015 | Jinadatha |
| 2015/0314026 A1 | 11/2015 | Mauzerall et al. |
| 2016/0171179 A1 | 6/2016 | Donofrio et al. |
| 2017/0081707 A1 | 3/2017 | Dillon et al. |

FOREIGN PATENT DOCUMENTS

| | | |
|---|---|---|
| WO | 2016073634 | 5/2016 |
| WO | 2016130837 | 8/2016 |

OTHER PUBLICATIONS

U.S. Appl. No. 15/969,576, filed May 2, 2018.
International Search Report and Written Opinion dated Sep. 17, 2018 in PCT/US2018/038463.
International Search Report and Written Opinion dated Aug. 28, 2018 in PCT/US2018/038474.

INFECTION CONTROL APPARATUS

CROSS-REFERENCE TO RELATED APPLICATIONS

This application claims priority to, and the benefit of, U.S. Provisional Patent Application Ser. No. 62/524,320, filed Jun. 23, 2017, entitled INFECTION CONTROL APPARATUS, and U.S. Provisional Patent Application Ser. No. 62/524,313, filed Jun. 23, 2017, entitled INFECTION CONTROL METHOD, the disclosures of which are incorporated herein by reference in their entireties for all purposes.

FIELD

The disclosure generally relates to an apparatus usable for infection control. In particular, the disclosure relates to an apparatus that identifies critical control points in facilities and/or enables the spraying of those critical control point surfaces with a residual self-sanitizing coating to control the spread of infection.

BACKGROUND

Nosocomial infections, "hospital acquired infections" and/or "healthcare associated infections" (HAIs) are infections that otherwise uninfected patients sometimes acquire when receiving medical treatment in a healthcare facility. The U.S. Centers for Disease Control (CDC) estimates that HAIs account for about 1.7 million infections and 99,000 related deaths per year.

The cause of HAIs is often cross-contamination in the hospital. For example, when an improperly sterilized medical device (e.g., an endoscope) or improperly disinfected equipment (e.g., bedrails or x-ray machines) remain contaminated with pathogens and then are placed in contact with an otherwise uninfected patient. Although causation may be obvious, mitigating the problem is often not so simple. Without knowing the specific equipment that was contaminated, countless pieces of equipment would need to be randomly and almost continuously cleaned and sanitized. Such a cleaning effort would take enormous resources, leaving even less time for actual medical procedures. Further, even surfaces identified as presently contaminated may be contaminated again just moments after cleaning and sanitizing the surfaces, resulting in the whole process being futile.

The foodservice industry also has its share of disease, such as in the form of food borne illness. One program exists to identify where in a food service establishment the likely sources of contamination exist. The program is referred to as HACCP (Hazard Analysis and Critical Control Points) and is a systematic preventative approach to food safety. However, the program, although diligent and structured, merely identifies the obvious ways to control pathogens, namely employee hand washing and the rigorous separation between uncooked and cooked foods before, during and after preparation.

In spite of the recent diligence to reduce the HAIs problem in the healthcare profession, and the existence of the HACCP preventative approach to pathogen control in the foodservice industry, what is still needed in both healthcare and foodservice is a system and method for identifying where pathogens reside in a facility at any given time. Moreover, a need exists to know which surfaces are the critical transfer points based on actual pathogen presence and transfer routes. Further, the need still exists for improved methods for coating such contaminated surfaces once identified such that pathogen transfer over time is eliminated entirely.

SUMMARY

An apparatus for controlling infections is provided. In various embodiments, the apparatus mitigates HAIs in hospitals and other healthcare facilities by targeting critical control points in the facility. In various embodiments, an infection control apparatus comprises: (i) a computing unit, (ii) an asset tagging unit, (iii) a spraying unit, (iv) a power supply unit, and, in various embodiments, (v) optionally a DNA/RNA sequencing unit. In general, the apparatus is used to identify and treat critical control surfaces in facilities. More specifically, the infection control apparatus enables (a) detection and identification of pathogens on various stationary or movable assets within a facility, (b) tracking asset and pathogen movement around the facility, (c) determination as to which asset surfaces are critical control points based on pathogen counts, genetic mutations and/or movement routes over time, and (d) coating of those surfaces with a residual self-sanitizing coating composition that provides a coating on the asset surfaces to continuously destroy pathogens. In this way, the present infection control apparatus shuts down pathogen transfer routes by ensuring no pathogens, or only a minimal number of pathogens, such as a non-pathogenic level of organisms, can survive on the critical control surfaces.

In various embodiments, an infection control apparatus comprises: an asset tagging unit; a spraying unit; a power supply unit; and a computing unit comprising a non-transitory computer-readable medium encoded with program instructions for controlling the asset tagging unit and the spraying unit to perform a method of infection control in a facility. In various aspects, the infection control apparatus further comprises a DNA/RNA sequencing unit controlled by the program instructions. In certain embodiments, the encoded program instructions also control the power supply unit of the apparatus.

In various embodiments, the infection control apparatus further comprises a cabinet physically enclosing at least a portion of the apparatus, such as to hide and protect equipment such as a computer CPU, hose reels and chemical storage tanks. The cabinet may include a set of wheels to mobilize the apparatus as a cart and any number of doors to access the interior of the cabinet. The apparatus may also comprise external indicia positioned outside of the cabinet and controlled by the program instructions, and the external indicia may further comprise an LED screen or various indicator lights that signal various events.

In various embodiments, the computing unit of the infection control apparatus comprises a desktop computer, a laptop computer, or a tablet.

The asset tagging unit may further comprise an RFID reader and a plurality of RFID tags, each tag readable by the RFID reader and each tag associated with an asset located inside the facility, wherein the program instructions further comprise RFID asset management software that provides instruction to the RFID reader.

In various embodiments, the apparatus may further comprise a plurality of RFID readers stationed around the inside of the facility capable of obtaining and transmitting the location of each one of the plurality of RFID tags to the non-transitory computer-readable medium upon command from the RFID asset management software. In this way, inventory of assets around the facility is automated electronically.

In simpler embodiments, the asset tagging unit may comprise a barcode printer, a barcode reader, and a plurality of barcode labels printed by the barcode printer, each label readable by the barcode reader and each label associated with an asset located inside the facility. In this way, inventory of assets in a facility is more of a manual process, e.g. for someone to venture around the facility and read barcodes.

In various embodiments, the spraying unit further comprises a tank module and a spray module. In some instances, the tank module further comprises at least two tanks, each tank further comprises at least one of a weight sensor, a liquid level float, and an optical sensor controlled by the program instructions. In this way, weight or volume loss in a chemical storage tank can be electronically determined and recorded.

In certain aspects, the spray module comprises (i) at least one spray gun; (ii) an air compressor and at least two compressed air supply lines, each compressed air supply line connecting the air compressor and each of the at least two tanks in fluidic communication to pressurize each tank; and (iii) at least two chemical supply lines, each chemical supply line connecting one of the at least two tanks and the at least one spray gun in fluidic communication. The compressed air supply lines and the chemical supply lines in this case may be managed on retractable hose reels for neatness and convenience.

In other embodiments, the spray module comprises a fluidic pump having an inlet and an outlet, a spray gun, a chemical supply line, and a switchable valve controlled by the program instructions, wherein the at least two tanks are in fluidic communication with the switchable valve, the switchable valve is in fluidic communication with the inlet of the fluidic pump, and the chemical supply line provides fluidic communication between the outlet of the fluidic pump and the spray gun. In this case, the chemical supply line may be managed on a retractable hose reel.

In various embodiments, a method of infection control in a facility containing a plurality of assets capable of changing locations within the facility is disclosed. The method comprises: providing the infection control apparatus described above with its computer controlled asset tagging unit and spraying unit, power supply unit and optional DNA/RNA sequencing unit; creating a unique asset record for each asset; associating each asset record with a unique asset identifier comprising either a printed barcode label or an RFID tag; physically tagging each asset with its associated asset identifier by attaching the barcode label or the RFID tag to the asset; swabbing a surface of each asset with a surface testing swab to obtain a measure of pathogen contamination on the surface of the asset; obtaining the location of each asset; inputting the location of each asset and the measure of pathogen contamination on the surface of the asset to the computing unit as a first set of data; repeating the swabbing and obtaining steps for each asset after a period of time, and inputting the location of each asset and the measure of pathogen contamination on the surface of the asset to the computing unit as a second set of data; analyzing the data sets to determine which assets meet predetermined criteria to be categorized as critical control points within the facility; and spraying each asset categorized as a critical control point with a residual self-sanitizing coating composition delivered from the spraying unit.

In various embodiments of the method, obtaining the location of each asset may comprise instructing a plurality of RFID readers stationed around the inside of the facility to obtain the location of each RFID tag and to transmit the asset locations to the non-transitory computer-readable medium.

BRIEF DESCRIPTION OF THE DRAWINGS

The subject matter is pointed out with particularity and distinctly claimed in the concluding portion of the specification. A more complete understanding, however, may best be obtained by referring to the detailed description and claims when considered in connection with the following drawing figures:

DETAILED DESCRIPTION

Figure 1:
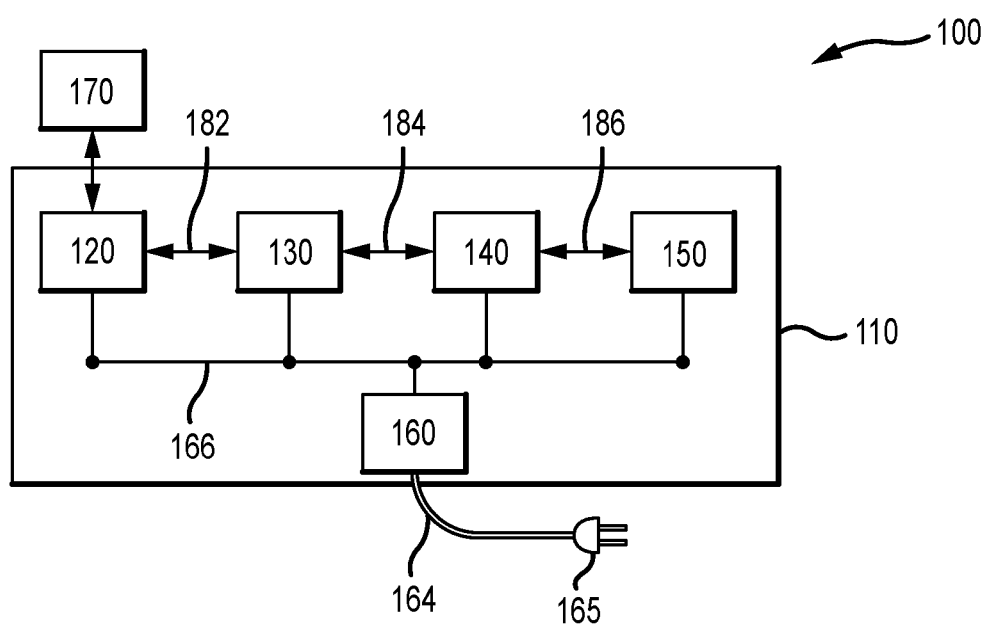
FIG. 1 schematically illustrates an embodiment of an infection control apparatus, according to various embodiments.

The detailed description of exemplary embodiments herein makes reference to the accompanying drawings, which show exemplary embodiments by way of illustration and their best mode. While these exemplary embodiments are described in sufficient detail to enable those skilled in the art to practice the invention, it should be understood that other embodiments may be realized and that logical, chemical, and mechanical changes may be made without departing from the spirit and scope of the inventions. Thus, the detailed description herein is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

In various embodiments, an infection control apparatus comprises: (1) a computing unit, (2) an asset tagging unit, (3) a spraying unit, (4) a power supply unit, and/or (5) a DNA/RNA sequencing unit. These units may communicate with each other and/or be connected together in any way such as, for example, electrically, electronically, as a network, for electrical power sharing, data transfer, and/or data sharing. The infection control apparatus may also comprise an enclosure (e.g., a cabinet) to contain at least some, or all, of the components of each of the above delineated units, and to keep everything together, organized and clean.

The infection control apparatus enables a method of infection control in interior environments (e.g., hospitals). The apparatus operates by identifying the critical control surfaces where pathogen transfers occur. The apparatus coats those surfaces with a residual self-sanitizing coating, so that the surfaces can no longer sustain (or have minimal) viable microorganisms at pathogenic levels. The apparatus identifies the critical control surfaces by, for example, tagging and tracking assets in a facility, monitoring microbial counts and types of microorganisms on the assets over time, and/or processing these data to identify assets that are the "crossroads" for pathogen transfer. The apparatus may be used to spray those surfaces with a residual self-sanitizing coating composition, so that the surfaces can no longer participate in pathogen transfer. The apparatus economizes, simplifies and/or streamlines infectious disease control in a facility by identifying and/or treating only those surfaces determined to be critical control points, so that random, ineffective cleaning and disinfection protocols can be reduced or eliminated.

Definitions and Interpretations

As used herein, the term "asset" broadly refers to an object comprising at least one hard inanimate surface (an environmental surface, or fomite), which is located within an interior environment such as a healthcare facility, bus station, train station, airport, restaurant, food service provider, and the like. An asset may be portable and moveable, moveable but never moved or intended to be moved, or entirely fixed and stationary. Assets in a healthcare facility include, for example, beds, carts, trays, IV stands, bedside tables, door handles, portable medical equipment (EKG, X-ray, ultrasound, etc.), reception desk, chair armrests, and countertops.

Assets of interest may include those assets that are frequently touched and/or likely to be contaminated at any particular time. Other assets of interest include those that are moved between patient rooms, such as on a daily basis. Some assets may be so remotely located and so unlikely to be involved in pathogen transfers (e.g. a shelf in an infrequently accessed storage room) that they may not be the target of any pathogen investigation. Assets of high interest are those that are likely to be contaminated, likely to be moved frequently, and/or that are handled frequently or placed into contact with a person, such as a person with an infection. Some assets that come into contact with one patient, such as a portable X-ray machine, are of interest since they could be involved in the movement of pathogens to another patient.

Assets may have a particular surface that is touched or that contacts a person and one or more other surfaces that are never in human contact. For example, a countertop asset will be frequently touched on the top surface and front edge, but rarely if ever underneath. Even though the asset may be of interest since pathogens could be transferred to and from the countertop, only the top surface and front edge may be of interest for microorganism monitoring. Further, some assets may comprise a combination of hard and soft surfaces. One example is a hospital bed that includes the adjustable bedrails, usually metal, which are frequently handled, and the bedding that is laundered and not easily monitored for microorganism presence over time. In this case, the asset is logged-in to the apparatus as "hospital bed," with a note that the surfaces of interest for pathogen transfer may be the metal rails. Another example is a chair, which is an asset having a soft surface (cushion) and hard surfaces (the armrests), and it is the latter that may be the surfaces of interest in pathogen transfer on this asset.

As used herein, the terms "crossroads" and "critical control points" are used interchangeably to refer to those surfaces of assets that are found to be pathogen transfer points. A critical control point may be referenced by the asset name for simplicity, even though only one surface of the asset may be involved in the transfer of pathogens. As discussed herein, the critical control points can then be treated with a residual self-sanitizing coating composition so that they can no longer harbor viable organisms at pathogenic levels. In this way, critical control points, once identified and coated, cease to be pathogen transfer "crossroads."

As used herein, the term "facility" refers to any interior environment of any size. Facilities include, but are not limited to, hospitals and healthcare buildings in general, restaurants, train stations, bus stations, airports, train, bus, plane, food trucks, office buildings, schools, churches, and the like. Although the present disclosure focuses on healthcare facilities such as hospitals, and exemplifies the control of HAIs in a hospital, the present disclosure is not limited to the healthcare industry or HAIs at all, and can easily be adapted to control the spread of infection in any of these other facilities.

As used herein, the term "pathogen" takes on the ordinary and customary meaning of microorganisms that cause infection in a host. Within the scope, pathogens of interest include those that cause human infections, and these generally comprise bacteria, viruses and fungi. Further, pathogens recognized as microorganisms that cause HAIs and known to transfer indirectly through contaminated surfaces are of interest within the scope of the disclosure. For example, pathogens that cause HAIs include, but are not limited to norovirus, poliovirus, rotavirus, influenza virus, adenovirus, *Staphylococcus aureaus*; methicillin resistant *Staphylococcus aureus* (MRSA); vancomycin resistant *Enterococcus* (VRE); carbapenem resistant Enterobacteriacea (CRE); *Listeria* spp.; *Klebsiella* spp.; *Pseudomonas aeruginosa; Acinetobacter* ssp.; *Bacillus anthraces; Salmonella* spp.; *Campylobacter* spp.; *Mycobacterium* spp.; *Streptococcus* spp.; and *Clostridium difficile*. Any one or more of these microorganisms, along with others now known or yet to be identified, may be responsible for infections spread within a facility, and thus controlling growth and spread of such microorganisms within a facility is a way to control infection in the facility.

As used herein, the acronym "CFU" or "CFU's" refers to "colony forming units," which in the field of microbiology refers to individual colonies of microorganisms counted on an agar plate. CFU is a measure of the level of contamination of a surface, whereby an agar plate is inoculated with a dilution of the microorganisms obtained from a test swab previously wiped on the surface to be tested. If the microorganisms are efficiently distributed on the agar plate, it can be generally assumed that each cell will give rise to a single colony, which can be counted. The counting of CFU's on an agar plate may be manual (e.g. assisted by a click-counter so as not to lose count), or may be electronic, such as by electrical resistance, flow cytometry, image analysis, or other method. Electronic methods for counting CFU's may be calibrated by hand counting. The appearance of each colony, (e.g. shape, color), can be indicative of the species of microorganism growing on the plate. Otherwise, a separate genetic test can be used to verify the identity of a pathogen.

As used herein, the term "antimicrobial" is used generally to indicate at least some level of microbial kill by a composition or a coating on a surface of an asset. For example, antimicrobial may be used to indicate a sanitizing level (3-log, or 99.9%) reduction in at least one organism, or a disinfection level (5-log, or 99.999%) reduction in at least one organism, or sterilization (no detectable organisms). Microorganisms may include any species of bacteria, virus, mold, yeast, or spore. The terms "residual antimicrobial," "residual self-sanitizing," and "self-decontaminating surface" are used interchangeably to indicate a hard inanimate environmental surface that maintains antimicrobial efficacy over a certain period of time under certain conditions once the surface is coated with an antimicrobial coating composition. A coated surface may maintain residual antimicrobial efficacy indefinitely, or the coating may eventually "wear out" and lose its residual antimicrobial efficacy. An antimicrobial coating composition may function as a contact sanitizer, disinfectant, or sterilant when first applied to a surface, and also have the ability to leave behind a residual antimicrobial effect on the surface once dried or cured thereon that can keep inactivating new microorganisms that contact the coated surface. In various embodiments, coating compositions may not be antimicrobial until dried or cured on an asset surface, but are still referred to as antimicrobial coating compositions because of their ability to produce a residual antimicrobial coating on a surface. Antimicrobial coating compositions for use in various embodiments may provide a residual antimicrobial efficacy to a surface of an asset, meaning that a microorganism later inoculated on, or that otherwise comes in contact with the coated asset surface, may experience cell death, destruction, or inactivation. The residual antimicrobial effect made possible by the coatings is not limited by a particular mechanism of action, and no such theories are proffered. For example, an antimicrobial effect measured on a surface may be the result of intracellular mutations, inhibition of certain cellular processes, rupture of a cell wall, immobilization and thus prevention of transfer or detection when swabbing, or a nondescript inactivation of the organism. Other antimicrobial effects may include inhibiting the reproduction of an organism, or inhibiting the organism's ability to accumulate into biofilms. In other embodiments, an antimicrobial effect may be a stasis such that organisms cannot proliferate to the point of reaching a pathogenic level on the treated surface.

As used herein, the term "antimicrobial coating composition" or "residual self-sanitizing coating composition" refers to a chemical composition comprising at least one chemical species, which is used to produce a residual self-sanitizing antimicrobial coating on an asset surface after the composition is applied and then either dried, allowed to dry, or cured in some manner. However, the term is extended to include a composition that may be applied sequentially (e.g. over or under) or contemporaneously with the application of an antimicrobial coating composition comprising an antimicrobial active, such as to assist in bonding the residual antimicrobial coating to the surface, improve durability of the overall coating, and/or to provide a catalytic effect or some sort of potentiation or synergy with the residual antimicrobial coating comprising an antimicrobial active. For simplicity herein, each one of multiple compositions used sequentially or contemporaneously to produce an overall residual antimicrobial coating on a medical implement or device is referred to as an "antimicrobial coating composition," even if one or more of the compositions used for coating has no identifiable antimicrobial active or where the active agent is uncertain. An antimicrobial coating composition may comprise a neat, 100% active chemical species or may be a solution or suspension of a single chemical species in a solvent. In other aspects, a composition may comprise a complex mixture of chemical substances, some of which may chemically react (hydrolyze, self-condense, etc.) within the composition to produce identifiable or unidentifiable reaction products. For example, a monomeric chemical species in an antimicrobial coating composition may partially or fully polymerize while in solution prior to a coating process using that composition. In various embodiments, chemical constituents within an antimicrobial coating composition may chemically react on the surface that the composition is applied to, such as while the composition is drying and concentrating on the surface or while the coating composition is cured by various methods. Antimicrobial coating compositions for use in various embodiments may further comprise any number and combination of inert excipients, such as for example, solvents, surfactants, emulsifiers, stabilizers, thickeners, free-radical initiators, catalysts, etc. Exemplary antimicrobial coating compositions that leave behind a residual self-sanitizing coating on a surface, and that are suitable for use herein, include, but are not limited to: a quaternary ammonium biocide/polymer complex exemplified in U.S. Pat. Nos. 6,017,561; 6,080,387; 6,270,754; and 6,482,392 assigned to The Clorox Company and incorporated herein by reference in their entireties; solutions of 3-(trimethoxysilyl) propyl dimethyl octadecyl ammonium chloride (CAS No. 27668-52-6, obtained under various trade names); SilverShield®, a coating that delivers antimicrobial silver over time and is available from Microban®, Huntersville, N.C.; and solutions and methods comprising various organosilanes, organic amines, titanium(IV) species, titanium sols, tartaric acid/titanium complexes, and combinations thereof, as exemplified in U.S. patent application Ser. No. 15/938,417 filed Mar. 28, 2018 and Ser. No. 15/969,576 filed May 2, 2018, both assigned to Allied Bioscience, Inc. and incorporated herein by reference in their entireties; in PCT International Patent Application Serial Nos. PCT/US13/073878; PCT/US15/059080; and PCT/US16/017599 assigned to Allied Bioscience, Inc. and incorporated herein by reference in their entireties; and in U.S. Pat. Nos. 9,963,596; 9,918,475; 9,856,360; 9,855,584; 9,757,769; and 9,528,009, assigned to Allied Bioscience, Inc. and incorporated herein by reference in their entireties. In various embodiments, the infection control apparatus is used to coat an environmental surface with either (a) a mixture of 3-(trimethoxysilyl) propyl dimethyl octadecyl ammonium chloride, 3-chloropropyltrimethoxysilane, and triethanolamine, remainder water; or (b) a mixture of 3-aminopropyltriethoxysilane and triethanolamine, remainder water. Either organosilane coating may be coated overtop with a titanium species, such as an aqueous mixture of $TiO_2$ or a sol that provides a film of $TiO_2$. In other embodiments, an environmental surface is first coated with a titanium species and then with either composition (a) or (b). In other embodiments, any other residual self-sanitizing coating, whether modifications of these quaternary and organosilane technologies, or comprising any other coating technology, are suitable for use in infection control as per the present disclosure.

Computing Unit

In various embodiments, an infection control apparatus comprises a computing unit. The computing unit comprises hardware, such as a computer-readable medium, and software instructions on the computer-readable medium, along with the necessary connection (hardwire/USB or wireless) to the other units in the apparatus. In particular, the computing unit can communicate with and control the asset tagging unit and any of its components, the spraying unit and in particular the spray module of that unit, and/or the optional DNA/RNA sequencing unit, by the appropriate hardwire/USB or wireless connections. Computing hardware may comprise a computer running on any platform, further comprising a CPU, memory (e.g. RAM and ROM), keyboard, monitor, mouse and peripherals as needed. In various embodiments, the computer comprises a non-transitory computer-readable storage medium encoded with instructions that, when executed by a processor in the computing unit, cause performance of specific methods, such as to take an inventory of RFID tag locations, to measure a duration of spray from the spraying unit, or to make a mathematical calculation such as to divide the weight of chemicals sprayed by the duration of spray. In this way, through program instructions encoded on a non-transitory computer-readable storage medium, the computing unit controls the functions of the other units of the infection control apparatus, including the asset tagging unit and the spraying unit, optionally the power supply unit, and also the DNA/RNA sequencing unit if present. The computing unit may have its own power supply, or may tap into power available from the power supply unit of the infection control apparatus. In various embodiments, the computing unit also controls the functions of the power supply unit of the apparatus, such as to direct power to other units in the apparatus as needed. In broader terms, the computing unit comprises a non-transitory program storage medium having program instructions for controlling the various units of the infection control apparatus to perform the method of infection control described herein.

A keyboard and mouse may be used to manually input data into the computer processor, such as inputting the names of each of the assets in a facility, the initial locations of each asset at the start of an infection control procedure, and measures of pathogen contamination of various assets at various times during infection control. Some data will need to be manually entered into the computer processor, such as a list of the assets to be monitored and the measures of pathogen contamination on each asset, whilst other data may be electronically and automatically transmitted from a peripheral device to the computer processor, such as the locations of assets comprising RFID tags sensed by local RFID readers stationed around the facility.

In various aspects, a computing unit need not be housed in a single housing, but instead may be spread around the infection control apparatus or include separate components. For example, the overall infection control apparatus may be housed in a single encasement, such as a cabinet with doors, and thus the components of the computing unit may be spread around both the inside and outside of the cabinet. In various embodiments, the keyboard of the computing unit may be outside the cabinet, e.g. on an external shelf mounted on the cabinet, whereas the CPU and memory components of the computing unit may be inside the cabinet, hidden and/or protected. In various embodiments, a computing system herein comprises a typical desktop computer, further comprising a desktop CPU, keyboard, monitor, and mouse. The power cord from the desktop computer may be connected to the power supply unit of the infection control apparatus, or it may extend from the apparatus to plug into an outlet independent of the apparatus.

In various embodiments, the computing unit may comprise a laptop computer or tablet. The computing unit may have multiple monitors, e.g. of different sizes, and one or more of these may be mounted directly on the overall housing of the infection control apparatus. The computing unit may further comprise external indicia (e.g., indicator lights of various colors) to alert users of events, milestones, or issues occurring during the infection control process. The computing unit may further comprise specialized peripherals, such as optical readers for sensing the CFU's on an agar plate. In various embodiments, a computing unit is able to accept manually entered microbiological data, such as the CFU counts found on assets over time.

In various embodiments, a computing unit of the infection control apparatus further comprises computer software, e.g. loaded on computer-readable media such as a local hard drive of the CPU and/or on the Cloud. The software comprises those programs required to enable the steps of the present infection control method. In various embodiments, the software comprises database software capable of managing large sets of data. For example, a database program may provide fields for information regarding each asset in a facility, and these fields may be automatically filled in (e.g. date and time of day), manually filled in (e.g. entering in data from a keyboard), and/or electronically filled in upon a command, (e.g. RFID tag locations in an automated asset inventory procedure). Software may further comprise programs for enabling asset tagging, such as to coordinate barcode scanning with the database asset records, or to operate barcode label printers and/or RFID readers and remote sensors. Software may further comprise asset management and tracking software, which may be a retail software program used in other industries such as shipping and warehousing. In certain embodiments, software may comprise software for enabling a spraying unit, e.g. including a spray module with automated computer controlled valves and sensors, and to enable an optional DNA/RNA sequencing unit. Other software may include network software and algorithms to organize asset data entries and incoming data transfers, to facilitate communication between units and modules in an apparatus, and to calculate certain parameters as needed. The computing unit may further comprise software that records spray duration times from the spraying unit when that unit is actively used for spraying chemicals.

In various embodiments, the CPU further comprises an algorithm to process all the imputed data. Inputted data includes, but is not limited to, the asset tracking data, which is the location of the assets over time, and the microbial data, which comprises measures of pathogen contamination on each asset over time. The measures of microbial contamination of an asset are determined by swabbing surfaces of an asset, performing serial dilutions from the swab, inoculating agar plates, incubating agar plates, and counting CFU's on the plates. The CFU's give a measure of the original contamination that was on the asset surface. This data is likely entered into an asset record manually. Optionally, the microbial data further comprises DNA/RNA sequencing data for particular microorganisms on various assets, obtained for example from a DNA/RNA sequencing unit and transferred to the CPU for analysis.

The computer implemented analysis by the CPU comprises an analysis of data sets (each data set comprising asset location and measure of pathogen contamination on the asset at a particular time) to find those assets meeting predetermined criteria to be categorized as a critical control point within the facility. The algorithm takes into consideration the pathogen counts on assets over time, how the assets moved about the facility over time, and how pathogens in one place in the facility relate genetically and generationally to pathogens found in another place in the facility. When DNA/RNA sequencing is enabled, e.g. through a DNA/RNA sequencing unit, the genetic make-up of the pathogens can be used by the algorithm to determined the extent of mutations between instances of the same organism, and thus how long the organism has existed, how far it has been transferred, and if the pathogen has in fact been physically transferred by remaining viable on an asset that has been relocated in the facility. The CPU generates a report that comprises a list of assets identified as critical control point, i.e. those assets that meet the predetermined criteria. Once the assets are identified as critical control points by the CPU algorithm, then those assets are sprayed with a residual self-sanitizing coating composition by the appropriate spraying unit.

Asset Tagging Unit

In general, an infection control apparatus comprises an asset tagging unit capable of tagging assets so that their positions and movement around a facility can be tracked. Tracking of assets may be manual (such as by barcodes that include close-up and focused scanning) or real-time (such as by RFID tags), as explained herein. In some aspects, asset tagging comprises an asset management and tracking system further comprising hardware and software, such as used for tool and equipment check-in/check-out inventory, shipping/receiving and warehousing, pallet tracking, and general asset management in many industries. In various embodiments, asset tracking data are entered into or sent to the computer processor where the data are used, in part, to identify the critical control points in a facility, i.e. those surfaces where pathogens are being transferred to and from to cause an infection in the facility.

At the start of an infection control procedure there may be no assets logged into the database of the computer processor. Thus, each asset of interest in infection control can be logged into the database by name and/or by description of the asset, optionally including a picture of the asset. The information on the asset may be entered into the database using a keyboard. Further information that may be added into each asset record includes, but is not limited to, the shape and size of the asset, the surface area of touched surfaces on the asset, the temperature and relative humidity of the area surrounding the asset initially, and so forth. Then as each asset is physically tagged, such as by attaching a printed barcode or RFID tag onto the asset, a unique identifier such as the barcode number or RFID address can be associated with the asset record in the database. In this way, each asset becomes a record in the database, and additional information can be added to each asset record over time as needed. For example, the initial location of each asset may be entered into the appropriate field of each record as each record is created. An initial measure of pathogen contamination found on the asset can also be entered into each record. The location of the asset and the measure of pathogen contamination on the asset are then updated for each asset after passage of predetermined time periods.

In various aspects, an asset tagging unit comprises a barcode printer, printable labels, a barcode scanner, and barcode software. Both the hardware (printer, scanner and labels) and the software for asset management are available from, for example, Wasp Barcode Technologies, Inc., Plano, Tex., amongst other suppliers. The barcode software may be located on the CPU of the infection control apparatus rather than on a separate computer, such as a laptop or tablet. In various embodiments a portable barcode printer may be taken to the location of certain assets along with a laptop or tablet, such as when the asset is too large to move (e.g. an X-ray machine) or is stationary (e.g. a countertop at a nurse station), and/or when computers and equipment (e.g. configured as a cart on wheels) cannot be easily moved to the asset (e.g. an obstructed route). In various embodiments, the asset can be moved to the infection control apparatus for tagging, or the apparatus is moved to the asset for tagging, or a portable printer and laptop or tablet are brought around the facility. In various embodiments, one or more barcode labels are printed out and the barcode labels are simply walked over to the asset where they are applied.

Asset tagging facilitates tracking where the tagged assets are located in the facility at any given time. Once selected assets are barcoded, the barcodes on the assets may be scanned on a predetermined schedule (such as daily or another schedule, such as after each time period $t_1$, $t_2$, $t_3$, and so forth) and the scanned data, in conjunction with the initial location of the asset at $t_0$, is used to map where the assets have moved to, if they were moved at all. In various embodiments, rooms in a facility may be inventoried on a particular day and each barcoded asset present in the room scanned so that all the tagged assets can be logged-in as being in that particular room on that particular day. In other examples, an asset barcode may be scanned when the asset is moved and then scanned again at its destination. The process of tagging assets comprises choosing an asset from a list of assets to be tagged that are inputted into the barcode software, printing a unique barcode on an adhesive label using the barcode printer, and then applying the barcode to the asset. Each barcode is unique and identifies the asset. Barcodes may be applied to inconspicuous places on an asset, such on the underside of a surface, or in a doorframe rather than directly on a doorknob, away from physical contact areas or the areas that may be sprayed with a residual self-sanitizing coating composition using the spraying unit of the apparatus.

As explained in detail herein, assets in a facility may be portable, such as carts, tray tables, portable X-ray machines, beds, and the like, or may be permanently stationary, such as a countertop at a nurse's station or the doorknob of a lavatory. Assets are tagged as a way to create a record of a surface that may carry pathogens and that may act as transfer points or "crossroads." Thus, considerations such as the frequency an asset is handled or touched can be more important than whether the asset moves. In other words, even a frequently touched stationary countertop may be the crossroads for pathogen transfer, i.e., a "critical control point," and in recognizing that possibility it is important to tag the countertop as an asset and monitor the extent and identity of pathogen contamination on the countertop over time regardless that the countertop is stationary.

In various embodiments, an asset tagging unit utilizes RFID (radio frequency identification). For example, an asset tagging unit comprises RFID tags (each with an embedded chip and antenna and optional battery), an RFID reader (a transmitter with associated antenna), and RFID asset management software. As per the barcode variation discussed, the RFID software may be within the computing unit of the infection control apparatus rather than within the asset tagging unit or on a separate laptop or tablet. RFID tagging provides real-time asset tracking 24/7. RFID tags are applied as per the barcodes, e.g. on assets suspected to be pathogen transfer critical control points, away from the frequently touched portions of the assets. In various embodiments, the type of RFID tag for a particular asset may be based, at least in part, on the nature of the asset to be tagged. For example, some tags are designed to survive elevated temperatures, while others are designed for laundered fabrics. A wide variety of RFID tags is available, for example, from HID Global Corporation, Austin Tex., amongst other suppliers.

In various embodiments, RFID tags on tagged assets herein may be active or passive, or any combination of these, such as depending on the location of assets and likelihood the asset may be moved considerable distances across a medical center. A passive RFID tag includes energy sent as RF from a reader, whereas an active RFID tag has its own power source, a battery, and can communicate with a reader at much further distances on its own power. As per the barcodes, the RFID tags can be scanned from time to time to determine where the tagged assets reside in the facility. Unlike barcoding though, a plurality of RFID readers, e.g. with wireless connection to the asset tagging unit of the infection control apparatus, may be positioned in various locations around a facility such that, regardless of where assets may move to in the facility, there will always be an RFID reader nearby to sweep up the signals from the nearby collection of assets. Thus, by way of a command signal from the infection control apparatus, all of the tagged assets in the facility can be inventoried simultaneous by way of the remotely positioned readers without the need for anyone to walk around with portable RFID readers.

In various embodiments, the asset tagging unit of the infection control apparatus comprises hardware and software that is somewhere between barcodes and RFID tags in sophistication and convenience. An example is NFC (near field communication) asset tracking. With NFC, the scanner does not need to focus precisely on a barcode for reading. However, NFC cannot be used at any distance, and groups of assets cannot be scanned at the same time as per RFID. In other instances, the asset tagging unit of the infection control apparatus may comprise any other asset management and tracking system besides barcoding, RFID or NFC.

Spraying Unit

In various embodiments, the spraying unit enables any one of manual spraying, compressed air spraying, electrostatic spraying, and aerosol spraying. The spraying unit of an infection control apparatus further comprises a tank module, and a spray module that is in fluid communication with the tank module. In general, the tank module stores and supplies chemicals to the spray module, and the spray module enables the spraying of chemicals from the tanks onto the previously identified critical control points in the facility. Most of the spraying unit, including for example the entirety of the tank module, can be contained within an overall housing that encloses the infection control apparatus, such as a cabinet. However, certain portions of the spraying unit, particularly portions of the spray module, may need to reside at least temporarily outside the housing encasing the apparatus so that assets in the facility can be conveniently sprayed. For example, compressed air supply lines, chemical delivery hoses, spray guns and other components may be extendable away from the rest of the apparatus for ease of use. These portions of the spray module may then be retracted back or dismantled and placed back inside the overall housing of the apparatus when no longer in use.

The function and purpose of the spraying unit is to coat assets in the facility with a residual self-sanitizing coating composition and to measure the amount of material dispensed onto the various surfaces. In various embodiments, more than one composition is included per surface, or a repetition of one composition per surface. In other cases, a mixture of compositions may be applied to a particular asset surface. The spraying unit enables all of these combinations of product selection and dispensing, and the weights and timing measurements necessary to accurately record the amount of coating applied to various assets.

A. Tank Module

In various embodiments, the tank module comprises one, two, three, four or more tanks, each suitable for liquid storage and, in particular, for the storage of one or more residual self-sanitizing coating compositions that may comprise solvents and chemicals that attach or otherwise bond to various materials. A tank herein may be fashioned of any suitable material that is able to contain liquids and that is chemically compatible with the compositions contained therein, such as plastic, glass, or metal, and may further comprise a removable closure for refilling purposes. In various embodiments, a tank may comprise a bag-in-a-box package, or a standard pail with a bung that can be tapped. In other examples, a tank herein may comprise an aerosol package further comprising a liquid and an aerosol propellant (discussed in more detail herein). A tank may be of any capacity, such as for example, from about 0.5 liter capacity up to about 40 liter. The capacity of a tank in the tank module may depend on a number of considerations, such as, how many tanks are included for an embodiment of the infection control apparatus, the nature of the liquid materials in the tank, (e.g. as relating to the amount of material typically sprayed on a surface), whether the tank is refillable or not refillable and disposable, the overall weight of the infection control apparatus, and how portable the apparatus needs to be, amongst other considerations. For example, an infection control apparatus may comprise a spraying unit with only one 30 liter tank, whereas another infection control apparatus may comprise a tank module comprising three 10 liter tanks. In another example, a spraying unit comprises four, five or six, or more, 500 mL disposable aerosol cans. Aerosol cans may be designed to plug into the spraying module, such as with the aerosol stem fitting into an appropriately dimensioned socket in the spray module. In various embodiments, an individual tank within the tank module further comprises at least one of a weight sensor, a liquid level float, and an optical sensor to monitor changes in weight of the tank or changes in the liquid level line inside the tank. In various embodiments, the weight sensor, liquid level float, or optical sensor is controlled by the program instructions encoded on the non-transitory computer-readable medium.

B. Spray Module

In various embodiments, the spray module comprises all the spray components necessary for any one of manual spraying, compressed air spraying, electrostatic spraying, or aerosol spraying of chemicals residing in the tank module. Exemplary spray modules herein minimally comprise a chemical delivery hose suitable for liquid flow and a spray gun in fluid communication with the tank module of the apparatus. In various embodiments, portions of the spray module are extendable away from other portions of the infection control apparatus, such as to allow for spraying of surfaces that are several feet or yards away from the apparatus. Thus, in several embodiments, either or both of a compressed air supply line and a chemical delivery hose can be disposed on a retractable hose reel such that either or both can be pulled out when needed and retracted back when not needed. The length of these two lines can be any length, such as from just a foot or so up to several hundred feet. Depending on the desired mode of spraying enabled by the spraying unit of the apparatus, only a chemical delivery hose may be connected to a spray gun. In other examples, both a chemical delivery hose and a compressed air supply line may be connected to a spray gun. In general, an electrostatic spray gun, although including both of these, does not require a third line to the spray gun, i.e. an electrical cable, because an electrostatic spray gun generally comprises an internal turbine operated by the compressed air, and this turbine produces the electricity supplied to the electrode needle of the spray gun.

Regardless of what type of spraying the spray module comprises, various on/off sensors and switches, weight sensors, liquid level floats, optical sensors, and the like, may be employed to enable recordation of chemical spray times and/or the amount of material dispensed from a tank during a spraying session. These data are sent to the computing unit where the coating data for a particular asset, e.g. one identified as a critical control point, is recorded for that asset. For example, a decrease in weight in a tank of chemicals can be measured while another sensor records the duration the spray gun is actuated in spraying the chemicals. The computing unit can then mathematically calculate amount/time, such as grams/sec of spray application. Additional data may be entered into the computing unit, such as the dimensions of the surface being coated. These dimensions may have already been entered earlier when the asset was logged into the database for the first time. When an asset is sprayed with a residual self-sanitizing coating composition, the computing unit may provide to the operator a measure of weight of composition per unit of surface area for the treated asset. The units for extent of coating may be $mg/cm^2$ or any other suitable units that indicate how much product has been sprayed on the asset surfaces per unit of surface area. Although these real-time measurements refer to the "wet" composition, the computing unit can calculate the expected weight of dry coating as weight per unit surface area based on the known actives percent of the composition sprayed. That is, data regarding the percent volatiles for a particular composition can be entered into the computing unit such that when an asset is sprayed, the computing unit can provide both the amount of material sprayed in real time (the "wet" amount) and the amount of dried coating expected on the asset once the surface dries, (i.e. by multiplying the amount of wet composition sprayed per unit of surface area times the percent actives of the composition).

In various embodiments, and depending on the particular compositions used, the type of spraying, and other considerations, the coating of a surface of an asset identified as a critical control point may be from about 1 $\mu g/cm^2$ up to about 500 $mg/cm^2$ of asset surface, after surfaces are allowed to dry.

All the components that may enable each of these modes of spraying are available, for example, from Finishing Consultants, Inc., Everett, Wash., amongst other suppliers.

Manual Spraying

In various embodiments, the spray module for manual spraying comprises a fluidic pump that moves chemicals from one or more tanks in the tank module through a chemical delivery hose and out to a spray gun. The pump may comprise any type of in-line fluid pump that can supply the liquid to be sprayed at a suitable pressure such that the liquid is aerosolized by the spray nozzle on the spray gun. In various embodiments, a spray module comprises two sections of chemical delivery hose with connectors at each end of both sections, a spray gun, and an in-line pump disposed anywhere between the spray gun and the tank, wherein one section of hose fluidically connects a tank of the tank module to the inlet of the fluid pump and the other section of hose fluidically connects the outlet of the fluid pump to the spray gun. The connectors may be of any type, such as for example, quick disconnect Swage-type fittings, or threaded connectors, or any other type of connectors for fastening hose to a hose bib. The chemical delivery hose may comprise any material that is reasonably flexible, such as plastic, and may comprise combinations of materials. For example, a chemical delivery hose herein may comprise a polyethylene tube surrounded by a stainless steel or other type of metal mesh for reinforcement. In this way, the metal mesh protects and reinforces the inner polyethylene tubing, extending its life. Other tubing can be selected depending on the corrosive nature of the chemicals to be sprayed, and include for example, polycarbonate and Teflon. The inside diameter of a chemical delivery hose herein is from about 0.25 inches up to about 2 inches.

The spray gun of the spray module for manual spraying further comprises a handle that actuates the spray nozzle by opening a fluid passageway between the chemical delivery hose and the spray nozzle. The handle may further comprise a sensor that detects when the handle is gripped or actuated and when then handle is released. In this way, a sensor disposed on the spray handle of the spray gun detects the length of time the spray gun is spraying. Data from the spray gun sensor can be transmitted back (e.g. wirelessly) to the computing unit of the apparatus where a software program logs the spray times into the record for the asset being sprayed.

Compressed Air Spraying

In various embodiments of compressed air spraying, the spray module may comprise a chemical delivery hose enabling fluid communication between a tank in the tank module and a spray gun as per the manual spraying option. In various aspects, compressed air spraying by the spraying unit herein is equivalent to commercial liquid spraying seen in the painting and finishing industry wherein the tank of liquid is pressurized rather than pumped out. In compressed air spraying, pressure in the tank of liquid forces liquid from the tank through a delivery hose to the spray gun where it is atomized by the spray nozzle. In various embodiments, the spray module further comprises an air compressor that pressurizes a tank in the tank module. A pressurized tank for liquid spraying is sometimes referred to as a "pressure pot." The air compressor may cycle on and off as necessary to maintain a constant pressure in the tank, such as up to about 100 psi. The air compressor may switch on automatically after a period of spraying that acted to reduce the pressure in the tank below a certain threshold pressure.

In other examples, a small reservoir or "cup" may be disposed on the spray gun, which can in various embodiments replace the need for a tank in the tank module altogether, or that can supplement the contents of a tank in the tank module with additional chemicals. A spray gun having a small cup such as having about a 0.5 L to about a 2 L capacity is somewhat analogous to commercial paint sprayers used in auto collision shops and other smaller scale spray operations. The spray unit may be configured with the tank module entirely remote from the spray gun, wherein a pressure pot is used as per large scale commercial spray systems. The pressure pot, the air compressor used to pressurize the pressure pot, and a hose reel may be contained and hidden inside the enclosure for the infection control apparatus, while the chemical delivery hose with the spray gun at the end can extend out from the enclosure. Alternatively, the tank module may comprise a small cup attached directly on the spray gun like a small paint sprayer, the contents of which are pulled out by the passing compressed air from a compressed air supply line. In that case, the air compressor and hose reel may be contained and hidden inside the enclosure of the infection control apparatus, while the compressed air supply line with the spray gun and liquid reservoir thereon can extend out from the enclosure. In further embodiments, a tank module may comprise both a reservoir cup directly on a spray gun and a tank such that the contents of the tank come out to the spray gun where the chemicals from the tank mix with the contents of the reservoir cup when the spray gun is actuated. In this case, both a chemical delivery hose and a compressed air supply line may be connected to a spray gun having its own reservoir cup.

It's important to note that chemical mixing can also be achieved by utilizing two or more tanks within the tank module and configuring the spray gun to draw upon the two or more tanks at the same time and at a prescribed mixing ratio. The tank module may further comprise a switchable valve to enable choosing one tank from two or more tanks present in the tank module, or for choosing to draw liquid from two or more tanks at the same time. For example, a 3-way "T-valve" in the tank module enables the choice between an "off position," connection between the spray gun and only a first tank, connection between the spray gun and only a second tank, or connection between the spray gun and both the first and second tanks. Various sized orifices may be placed in the valve or in the dip tubes extending into each tank such that a prescribed metering of chemicals to the spray gun is achieved, recognizing that the draw of liquid from each of two tanks may be configured to be different by placing different diameter orifices in each of the flow streams from the two tanks.

As per manual spraying with a similar or identical spray gun, the spray gun of the spray module further comprises a handle that actuates the spray nozzle by opening a fluid passage between the delivery hose and the spray nozzle. The handle may further comprise a sensor that detects when the handle is actuated and when then handle is released. In this way, the sensor on the spray handle of the spray gun detects the length of time the spray gun is spraying chemicals. Data from the spray gun sensor can be transmitted back (e.g. wirelessly) to the computing unit of the apparatus where a software program logs the spray times into the record for the asset being sprayed.

Electrostatic Spraying

In various embodiments, the spray module comprises an electrostatic spray system. Electrostatic spraying comprises positively charging the atomized liquid as it leaves the spray gun such that the atomized particles are attracted to a surface that is electrically grounded. Electrostatic spraying in a medical facility is promoted by the fact that many pieces of equipment are grounded, and that many frequently touched assets of interest regarding pathogen transfer (bed rails, IV stands, carts, etc.) are made mostly or entirely of metal. A spray gun suitable for electrostatic spraying may be manual or automatic electrostatic spray or low pressure or high pressure air-assisted electrostatic spray guns. For the spray modules herein, an electrostatic spray gun comprises two connections, one comprising the chemical delivery hose and the other comprising the compressed air supply line. The liquid chemicals to be sprayed may be supplied to the electrostatic spray gun by manual pumping (an in-line fluid pump) or from a pressurized tank.

In various embodiments, a spray module for electrostatic spraying comprises two sections of chemical delivery hose with connectors at each end of both sections, an electrostatic spray gun, an in-line pump disposed anywhere between the spray gun and the tank, wherein one section of hose fluidically connects a tank of the tank module to the inlet of the fluid pump and the other section of hose fluidically connects the outlet of the fluid pump to the spray gun, an air compressor, and a compressed air supply line with connectors at each end for providing compressed air from the compressor to the air inlet of the electrostatic spray gun. The spray module may further comprise two hose reels, one for retracting and managing the chemical supply hose and the other for retracting and managing the compressed air supply line.

In various embodiments, a spray module for electrostatic spraying comprises one section of chemical delivery hose with connectors at each end, an electrostatic spray gun, wherein the one section of hose fluidically connects a tank in the tank module to the electrostatic spray gun, an air compressor to pressurize a tank in the tank module, and a compressed air supply line with connectors at each end to bring compressed air from the air compressor to the air inlet of the electrostatic spray gun. The spray module may further comprise two hose reels, one for retracting and managing the chemical supply hose and the other for retracting and managing the compressed air supply line.

Aerosol Spraying

In various embodiments of the infection control apparatus, one or more residual self-sanitizing coating compositions may be provided in an aerosol package. Aerosol packaging comprises a liquid composition intimately mixed with a propellant and sealed in a can, usually metal, which is equipped with an actuatable valve. Another type of aerosol package comprises a "bag-in-can" concept wherein the liquid composition is in a bag and the propellant is in the can but outside the bag. An aerosol valve typically comprises a dip tube, a valve cup and a valve stem. Pressing down on the stem, or moving it laterally, causes the valve stem to open, whereby the pressurized mixture of liquid plus propellant is propelled up the dip tube and out the bore through the valve stem. Usually an aerosol package includes a button actuator that sits atop the valve stem, and which includes a nozzle insert that atomizes the liquid coming through the stem. For use herein, the button actuator can be eliminated, and the contents of the aerosol package may be directed out through a chemical delivery hose to a spray gun.

A spraying unit herein may further comprise a tank module comprising an aerosol package and a spray module comprising a fitting configured to accept the top portion of the aerosol package. In this way, one or more aerosol cans may be plugged into the spray module which controls actuation of the aerosol cans. For example, solenoids can be used for pressing down a fitting against an aerosol can to actuate a valve on the can. The spray gun may further comprise a switch and an electrical connection to the solenoid such that actuating the spray gun simultaneously operates the solenoid.

Power Supply Unit

In various embodiments, an infection control apparatus further comprises a power supply unit. In various embodiments, the power supply unit furnishes electricity to each of the components within each of the units using electrical power. In the simplest configuration, a power supply unit comprises an electrical "power strip" that plugs into an ordinary 110 v outlet. The power strip then supplies power to each of the devices through device power cords plugged into the strip. In other examples, the power supply unit comprises other components, such as a transformer. A 220 v power cord may extend from the infection control apparatus to a convenient 220 v outlet. The power supply unit may further comprise a 220 v/110 v transformer. In this way, the power supply unit is capable of supplying 110 v, such as to the computing unit, and 220 v, such as to the air compressor of the spray module. Thus, in various configurations, the power supply unit comprises any combination of an electrical cord, an electrical plug suitable for the chosen main supply voltage, a transformer, appropriate wiring, conduit, power strip, surge protectors, and cooling fans. All of these components except for the electrical cord and plug may be conveniently mounted within a cabinet the houses the majority of the infection control apparatus. Cooling fans may be mounted in holes through a panel of the cabinet, and the fans can cool the power supply unit components along with other devices closed up in the cabinet.

For operation outside the United States, the power supply unit is equipped with the appropriate electrical plug for the local electrical outlets, and is configured for the voltage of the local country.

Optional DNA/RNA Sequencing Unit

In various embodiments, an infection control apparatus may further comprise a DNA/RNA sequencing unit. Such a unit is optional because a microbial sample, obtained such as by swabbing a surface of an asset, can be sent to an outside laboratory for genetic sequencing, rather than performing this analysis on-site. Further, microbial samples may also be sent to a microbiology laboratory for colony counts, and the genetic sequencing could be done by the same laboratory. However, on-site genetic sequencing saves time in shipping the sample and waiting for the analysis, and the results of the analysis obtained on-site can be inputted directly and automatically into the computing unit of the infection control apparatus without the need for manual entry of the sequencing data. For infection control at a hospital or medical center, there will likely be a microbiology laboratory in the building or on campus that can perform the necessary dilutions, colony counts, and genetic testing from sampling swabs.

In various embodiments, an infection control apparatus comprises a DNA/RNA sequencing unit further comprising sequencing hardware and related software. Suitable DNA/RNA sequencers comprise nanopore sensors, and are available from Oxford Nanopore Technologies, Oxford, UK. In various embodiments, a DNA/RNA sequencing unit comprises a MinION, GridION, or PromethION sequencing device, from Oxford Nanopore Technologies. The MinION is a small portable sequencer, with flow cells containing up to 512 nanopore sensors. GridION is a larger sequencer that allows for integrated computing with up to 5 MinION flow cells. PromethION is larger, more like a benchtop piece of equipment, and designed to use up to 48 flow cells, each with up to 3,000 nanopore sensors. Any of these versions are suitable for the infection control apparatus herein, such as depending on a desired overall size for the apparatus, cost, and other considerations. These devices stream data in real time because DNA/RNA molecules are constantly moving through the micropore sensors. In other words, as one DNA/RNA molecule is passing through a micropore, other DNA/RNA molecules are loading into or coming out from other micropores. The analysis is run until a desired level of confidence is obtained, which is particularly suited for determining if a predetermined signature of interest is looked for in the DNA/RNA.

The DNA/RNA sequencing unit may be powered by an electrical connection, such as to the power supply unit of the apparatus, or may be powered by a USB cable connecting the DNA/RNA sequencing unit to the computing unit of the apparatus. The software provided with a commercial DNA/RNA sequencer may be loaded onto the computing unit of the infection control apparatus.

Additional Units

In various embodiments, an infection control apparatus may comprise further devices and equipment in addition to the units described herein. For example, an infection control apparatus may further comprise a dispenser for paper towels or wet wipes. In various embodiments, an infection control apparatus may comprise external indicia, such as audible horns, bells or ring tones, or visible indicator lights or beacons. The external indicia may be in addition to one or more monitors or LED screens that are part of the computing unit. External indicia may be used to signal to the user that an asset wasn't properly logged in, or that an asset record has not been updated with recent information such as its location or its pathogen colony count. Indicia lights may comprise green, yellow, and red indicator lights, such as to show levels of alarm for a particular issue that arises.

In various embodiments, an infection control apparatus may further comprise any necessarily equipment and supplies for on-board microbiological assays. For example, an infection control apparatus may comprise a box of swabs for swabbing surfaces of assets, bottles of buffer solution, pipettes and other laboratory equipment for sample preparation such as serial dilutions, agar plates, clicker counters, and automated CFU readers. The infection control apparatus may also comprise a small refrigerator or freezer, usable to store microbiological samples such as swabs before being sent out to a microbiology laboratory for analysis. In various embodiments, a refrigeration system may be used to keep one or more tanks of chemicals in the spraying unit under refrigeration. Other on-board equipment may include black lights to visualize biological materials on surfaces, and infrared or UV lights usable to cure various coatings on surfaces once sprayed with a residual self-sanitizing coating composition including a curing step. Other hand-held lighting may be used to activate a dye in a coating composition so that an operator can see if any residual self-sanitizing coating remains on a particular surface or if it has been worn off, such as by frequent touching.

In various embodiments, an infection control apparatus may include a cabinet, with any number of doors or other accesses. The cabinet may house the majority of the apparatus and help to keep the components clean and organized. As mentioned, a computer keyboard, computer monitor, various chemical delivery hoses and compressed air supply lines, a flow cell for DNA/RNA sequencing, a power cord and electrical plug, and external indicia such as indicator lights may all be outside the cabinet. In some examples, the infection control apparatus further comprises wheels to make the apparatus mobile. In various aspects, the apparatus is housed in a cabinet with wheels, like a mobile tool cabinet. Such a cabinet may be steel, or any other materials of construction, including combinations of materials. For example, plastic shelves may be employed inside a cabinet fashioned from sheet metal.

Specific Embodiments

Referring now to the drawing figures, FIG. 1 schematically illustrates an embodiment of an infection control apparatus 100, comprising a computing unit 120, an asset tagging unit 130, a spraying unit 140, an optional DNA/RNA sequencing unit 150, and a power supply unit 160. As shown, the infection control apparatus 100 may be housed in a suitable enclosure 110, such as a cabinet with any number of doors. The power supply unit 160 further comprises an electrical cord 164 and power plug 165 extending from the cabinet to the appropriate electrical outlet (e.g., 110 v or 220 v). The power supply unit 160 further comprises a common power strip 166 to provide electricity to each of the units 120, 130, 140 and 150 of the infection control apparatus 100. External indicia 170 may comprise indicator lights or other suitable alert system. As further illustrated schematically, the infection control apparatus further comprises the necessary data communications between the units. For example, computing unit 120 and asset tagging unit 130 may be electronically connected via data transmission lines 182. These data transfer lines 182, 184 and 186 do not need to be connected as shown literally. For example, each of the asset tagging unit 130, the spraying unit 140, the optional DNA/RNA sequencing unit 150, and the external indicia 170 may each directly communicate with the computing unit 120, rather than communicating to one another. As indicated previously, the computing unit 120 further comprises a non-transient computer-readable medium encoded with program instructions for controlling the other units, (e.g., 130, 140, 150, 160, and 170), of the apparatus to perform the method of infection control disclosed herein.

Figure 2:
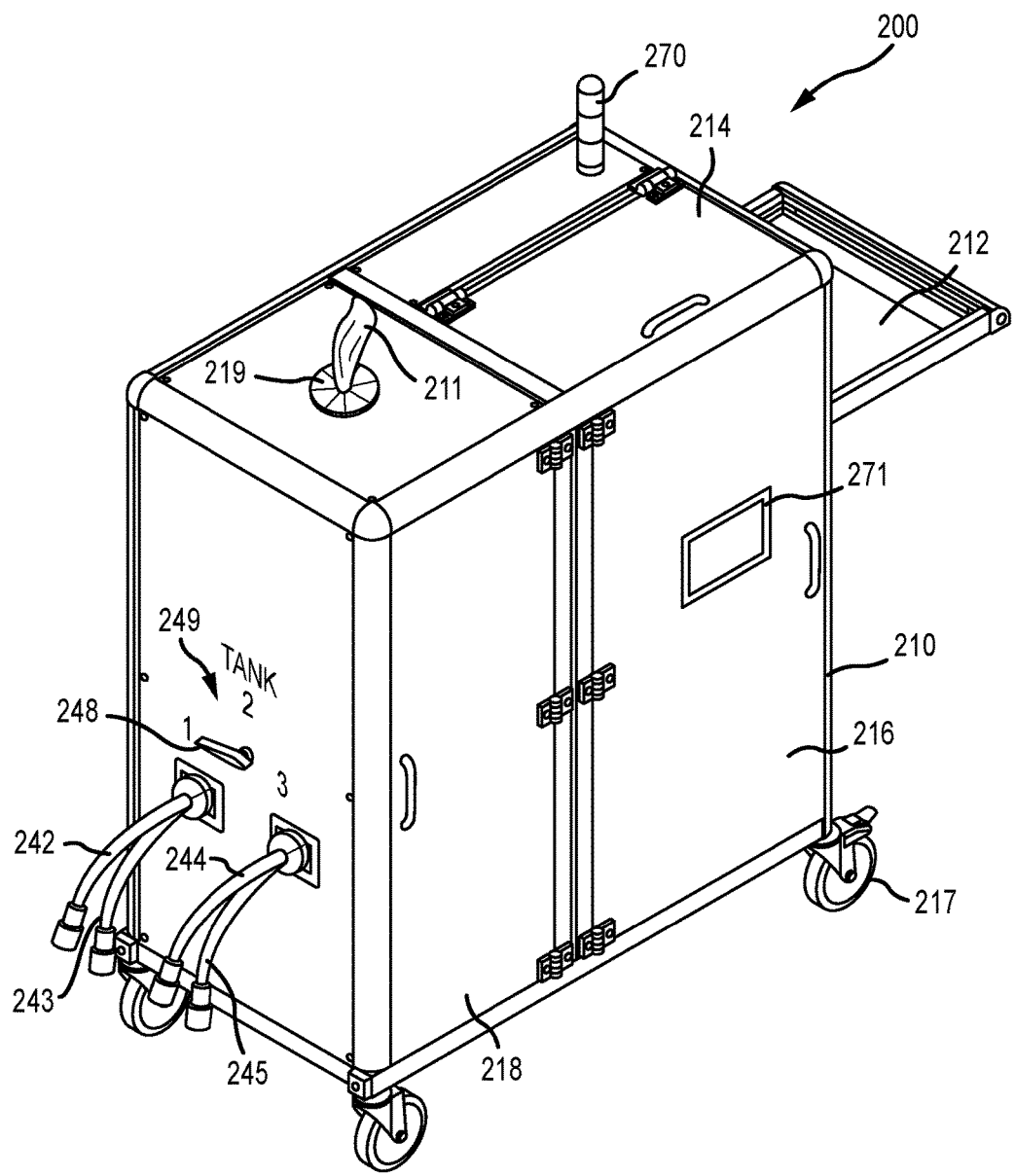
FIG. 2 illustrates a top perspective view of an embodiment of an infection control apparatus with each of the doors in their respective closed positions, according to various embodiments.

FIG. 2 illustrates a top perspective view of an embodiment of an infection control apparatus 200 in accordance to the present disclosure. The infection control apparatus 200 is shown embodied as a cart, comprising cabinet 210 set on wheels 217. Such a cart may comprise any number of wheels or castors. In this way the apparatus 200 is similar to a rolling tool cabinet seen in other trades. The apparatus 200 further comprises a shelf 212, which can be used to support a laptop computer or the keyboard and mouse from a desktop computer (with the CPU inside the cabinet 210, for example), a barcode printer, barcode scanner, RFID transmitter, spray guns, or any other componentry that may be more convenient to leave outside of the cabinet 210, even temporarily. The apparatus 200 may have any number of these shelves disposed anywhere on any side of the cabinet 210, or no shelves at all. Also, loose components, such as a barcode reader, may be placed on top of the cabinet 210 when in use, and then stored inside the cabinet 210 when not in use.

With continued reference to FIG. 2, the apparatus 200 further comprises any number of hinged doors on the cabinet 210. In this particular example, three hinged doors are provided, door 214, door 216, and door 218, with two on one side of the cabinet and one on top of the cabinet. These cabinet doors may have handles as shown and, in various embodiments, locks of any configuration. As shown, the apparatus 200 further comprises two different types of external indicia. The apparatus 200 comprises external indicia 270 which may further comprise indicator lights in any color, along with further external indicia 271, such as a small LED screen that can provide information, such as without having to turn on and boot the computing unit of the apparatus. The LED display 271 may show, for example, how full each chemical supply tank is, or even just the date and time of day.

As illustrated n FIG. 2, the infection control apparatus 210 further comprises two sets of chemical delivery hoses and compressed air supply lines. For example, one retractable set comprises compressed air supply line 242 and chemical delivery hose 243. Another retractable set of lines comprises compressed air supply line 244 and chemical delivery hose 245. There may be just one line, one set of lines, two sets of lines (as shown), or any number of retractable lines. Use of these supply lines is discussed herein in the context of the spray module of the spraying unit. The apparatus 200 further comprises a tank selection lever 248 attached to a valve assembly (not shown), and some type of indicia 249 to indicate the available positions of the tank selection lever 248. The valve assembly may be configured in many different ways, such as depending on how many supply tanks are available in the spraying unit, if an option to mix chemicals from two or more tanks is desired, and other considerations. For example, the valve and lever may be a standard 3-way "T-valve." Heavier and/or larger equipment, such as for example, an on-board air compressor, fluidic pumps, chemical delivery hose and compressed air supply line hose reels, and the like, can all be stored within the cabinet 210, toward any side of the cabinet, high or low in the cabinet, or in various positions within the cabinet, such as to accommodate and distribute the various size/weight of the components, electrical requirements, ventilation requirements, and other considerations.

As further illustrated in FIG. 2, the infection control apparatus 200 is shown to further comprise a wipes dispenser 219 configured through the top of the cabinet 210. Cleaning wipes 211 may be pulled from the dispenser 219 as needed, such as to wipe off assets prior to spraying or to clean up any drips from the spray gun or chemical supply lines, or simply for cleaning the computer keyboard and monitor, barcode reader, and other components that may be frequently handled. The canister of wipes (e.g. containing a continuous perforated roll of cleaning wipes) can be inside the cabinet 210 and hidden from view. This particular embodiment is not meant to be limiting as to the scope of other accessories the infection control apparatus 200 may comprise. The apparatus 200 may comprise any accessories, such as paper towel dispensers, fan folded paper towel dispensers, dry lens cloth dispensers, tissue dispensers, and the like, configured to dispense through slots, holes, or any other suitably shaped access ports provided through any side or top of the cabinet 210. In various embodiments, there may be nothing configured through the top of the cabinet 210 in this area, and wipes, tissues or other such supplies may simply be stored inside the cabinet 210 along with other equipment and supplies.

Figure 3:
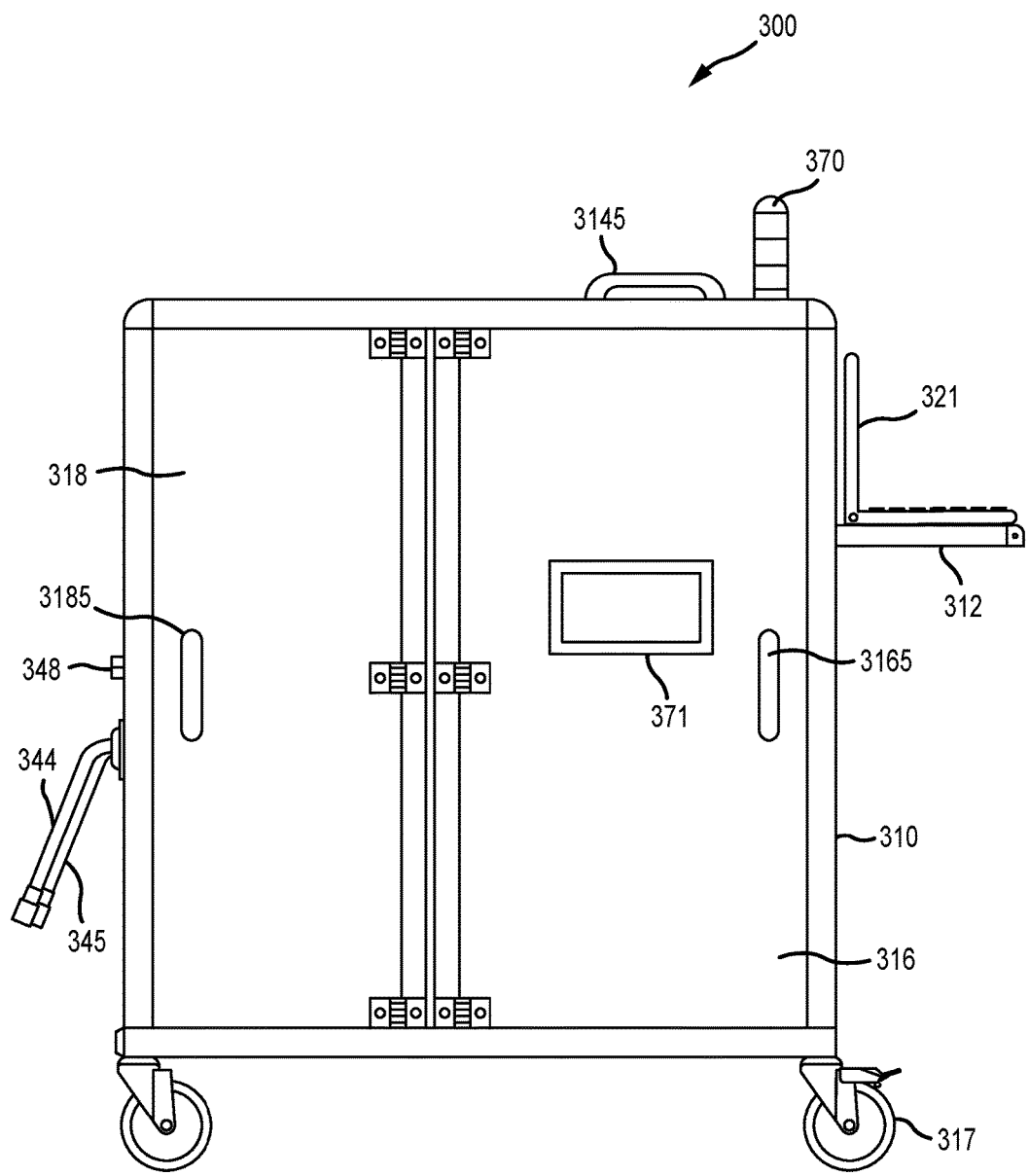
FIG. 3 illustrates a front view of an embodiment of an infection control apparatus with each of the doors in their respective closed positions, according to various embodiments.

FIG. 3 illustrates a front view of an embodiment of an infection control apparatus 300 in accordance to the present disclosure. As shown, the apparatus 300 comprises a cabinet 310, front cabinet doors 316 and 318, and is mounted on wheels or castors 317 so that the apparatus can be mobile. The door 316 is equipped with a door handle 3165, and likewise, the door 318 is equipped with a door handle 3185. The doors may be further equipped with locks or other accessories. External indicia 371, such as an LED screen, may be configured through one of the doors of the cabinet as shown, or at any other location. Further external indicia 370, such as one or more indicator lights, may protrude from the top of the cabinet 310 as shown, or may be disposed anywhere else on the cabinet 310.

The infection control apparatus also comprises a shelf 312, such as used for holding a laptop computer 321. As mentioned, the shelf 312 may also be used to support just the keyboard and mouse from a desktop computer, and perhaps the monitor, in which case the CPU may reside inside the cabinet 310, hidden from view and protected from dust and other environmental factors. A shelf such as 312 is optional, and may be positioned anywhere on the cabinet 310.

As further illustrated in FIG. 3, the infection control apparatus 300 comprises at least one set of supply lines, namely a compressed air supply line 344 and a chemical delivery hose 345. A switchable tank selection lever 348 allows choosing which chemical supply tanks in the tank module are in fluid communication with the chemical delivery hose 345.

Figure 4:
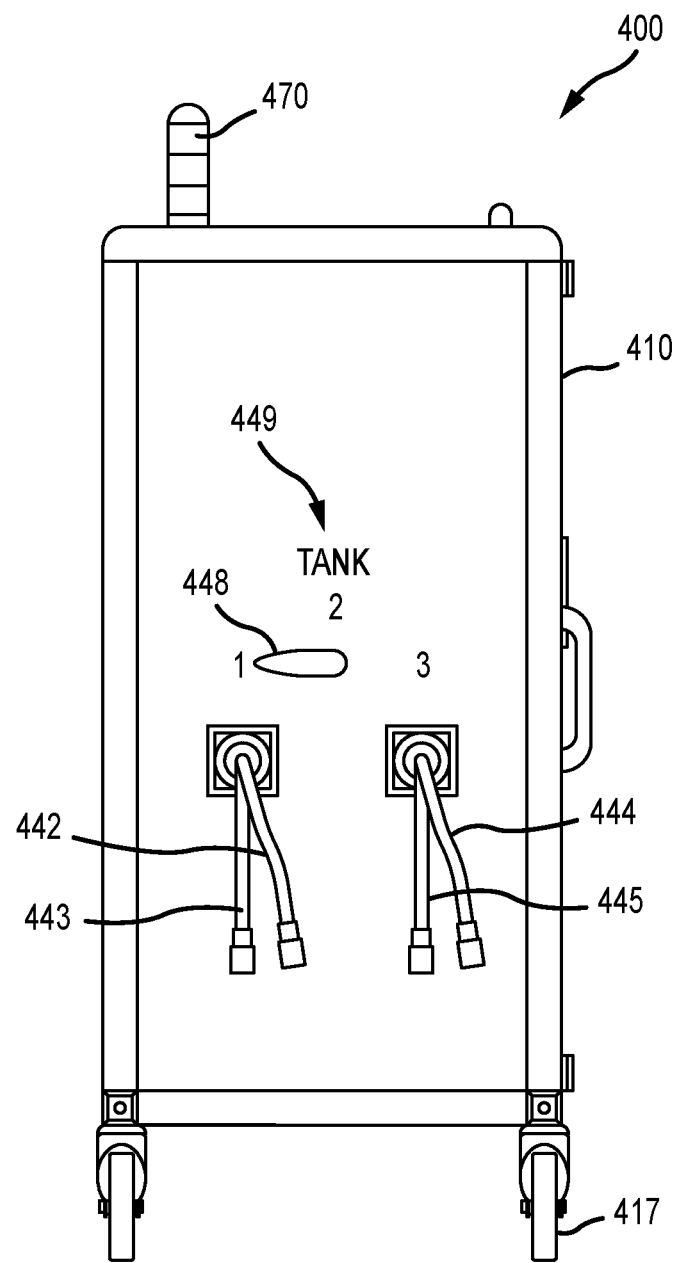
FIG. 4 illustrates a side view of an embodiment of an infection control apparatus, according to various embodiments.

With reference now to FIG. 4, a side view of an embodiment of an infection control apparatus 400 is provided. The apparatus 400 is enclosed in a cabinet 410, set on wheels or castors 417 such that the apparatus 400 comprises a mobile cart. The apparatus 400 further comprises external indicia 470 as mentioned previously. The infection control apparatus 400 also comprises two sets of supply lines. In this embodiment, the infection control apparatus 400 comprises one retractable set of lines comprising compressed air supply line 442 and chemical delivery hose 443. Another retractable set of lines comprises compressed air supply line 444 and chemical delivery hose 445. There may be just one line, one set of lines, two sets of lines (as shown), or any number of retractable lines. Use of these supply lines is discussed herein in the context of the spray module. Various spray guns that may be attached to these supply lines are not shown, and may be stored inside the cabinet 410 when not in use. Certain spray guns may include both a chemical delivery hose and a compressed air supply line, or just a chemical delivery hose. The apparatus 200 further comprises a tank selection lever 448 that operates a valve assembly behind (not shown), and some type of indicia 449 to label the positions of the tank selection lever 448 that may be selected. These labels are only an example, and it may be possible for a tank selection lever to choose more than one tank at the same time, rather than only tank 1, tank 2, or tank 3 individually.

Figure 5:
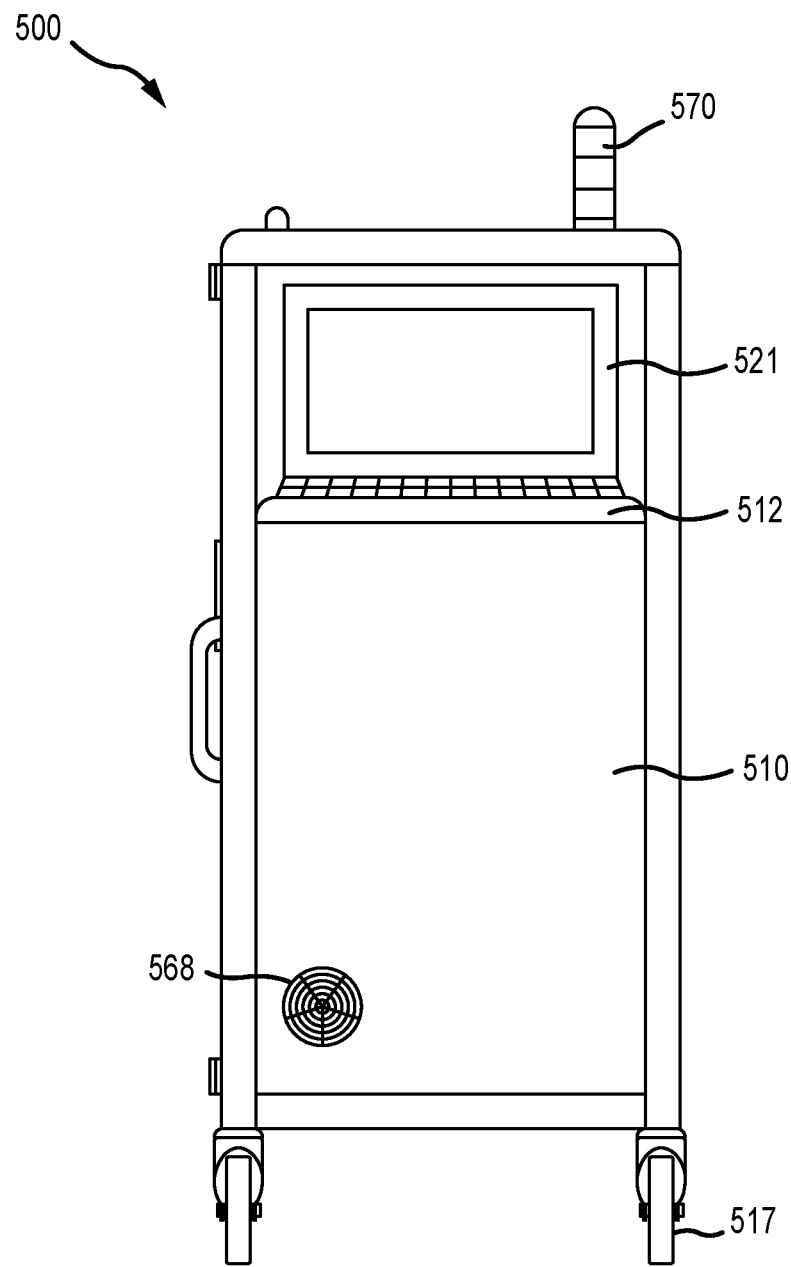
FIG. 5 illustrates another side view of an embodiment of an infection control apparatus, according to various embodiments.

FIG. 5 illustrates another side view of an embodiment of an infection control apparatus 500 in accordance to the present disclosure. The apparatus 500 comprises external indicia 570, such as a series of indicator lights or audible beacons. The apparatus 500 further comprises a shelf 512, on which a portion of the computing unit, here a laptop computer 521, may reside. In various embodiments, just the monitor, key board and the mouse from a desktop computer of the computing unit may reside on this supporting shelf 512. The infection control apparatus 500 may be enclosed in a cabinet 510 that is set upon wheels or castors 517 to enable movement of the apparatus 500. The apparatus 500 is also shown to comprise at least one ventilation fan, (the blades and motor of which are not visible in this view), which is evidenced by a wire grating 568 covering the opening through the cabinet 510, and protecting against contact with the blades of the fan. An infection control apparatus such as apparatus 500 may comprise any number of ventilation fans depending upon the equipment housed in the cabinet 510 and the ventilation requirements for these components. In various embodiments, equipment housed within the cabinet 510 will produce heat that can be dissipated out from the cabinet by way of these ventilation fans.

Figure 6:
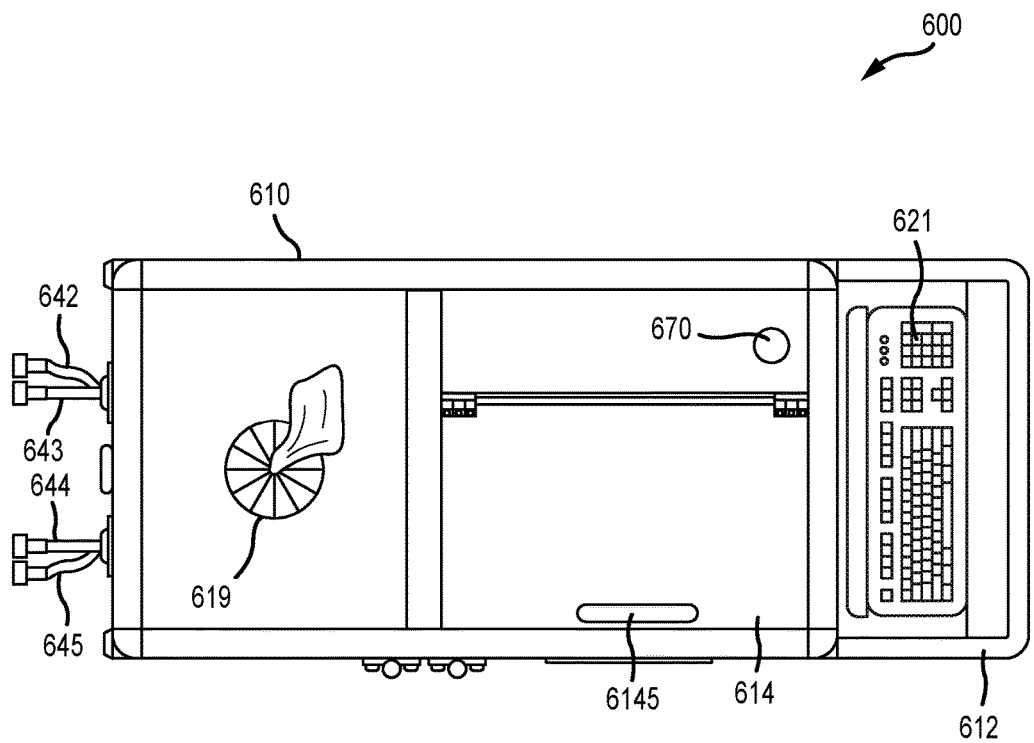
FIG. 6 illustrates a top view of an embodiment of an infection control apparatus with a door in its closed position, according to various embodiments.

FIG. 6 illustrates a top view of an embodiment of an infection control apparatus 600 in accordance to the present disclosure. The apparatus 600 comprises a laptop computer 621, external indicia 670, and a wipes or other towel or tissue dispenser 619. The apparatus 600 further comprises two sets of retractable supply lines. One retractable set comprises compressed air supply line 642 and chemical delivery hose 643. Another retractable set of lines comprises compressed air supply line 644 and chemical delivery hose 645. The apparatus 600 is shown enclosed in a cabinet 610, which further comprises a top door 614 with door handle 6145 for opening the door. Supply tanks within the tank module of the spraying unit may be accessible through door 614, or in other configurations, the door 614 may lead to any other portions of the infection control apparatus 600.

Figure 7:
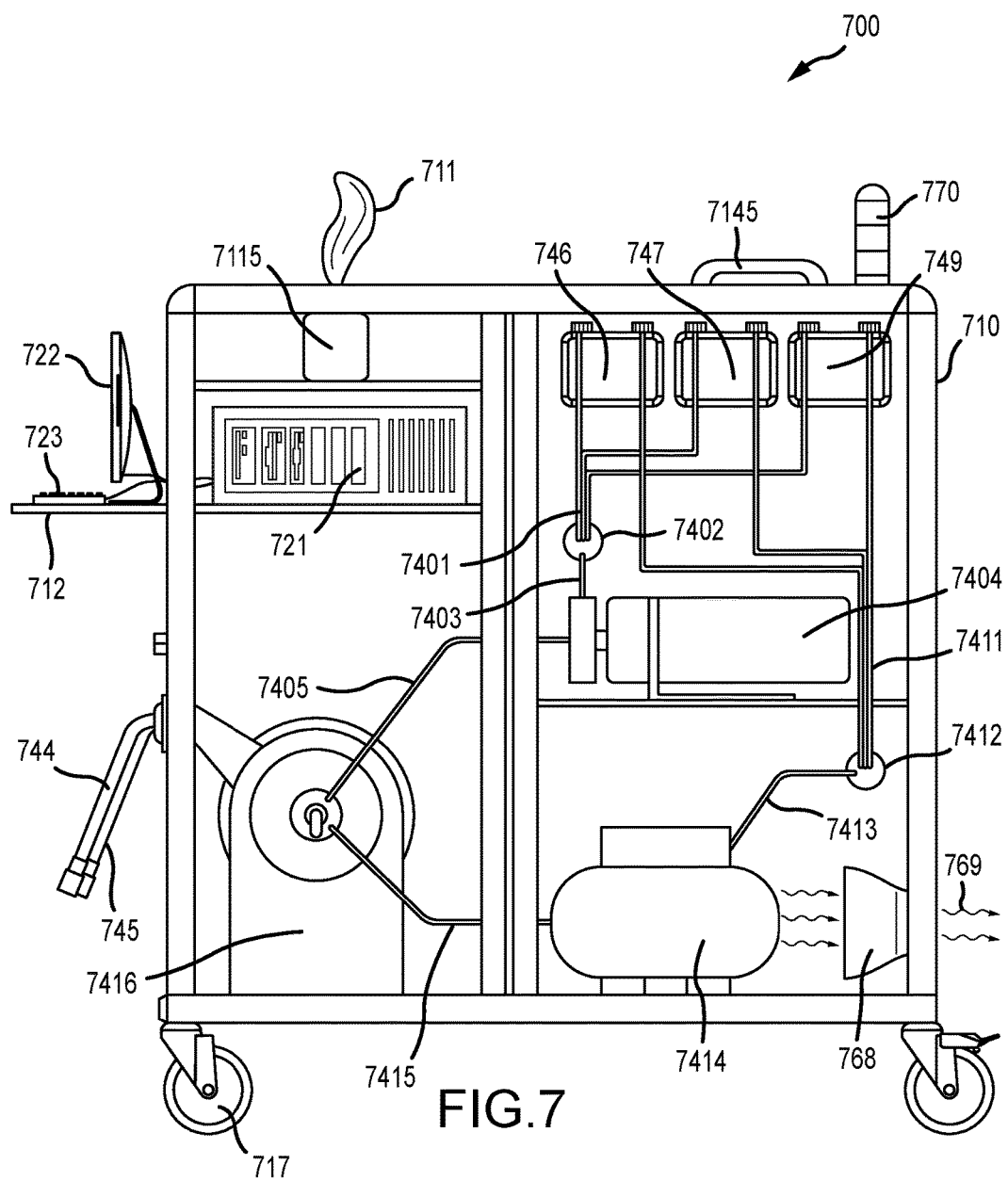
FIG. 7 illustrates a front view of an embodiment of an infection control apparatus with doors removed and contents exposed, according to various embodiments.

With reference now to FIG. 7, a front view of an embodiment of an infection control apparatus in accordance with the present disclosure is illustrated. The apparatus 700 is shown enclosed in a cabinet 710 with the doors removed such that the contents of the cabinet can be seen. Some of the details of the apparatus 700 are not illustrated and/or are not numerically labeled in this drawing for simplicity sake, such as for example, any electrical cords or conduits powering the various components, and any data transfer lines, such as USB cables between switchable valves, external indicia, equipment, or other computer controlled devices and the computing unit. This rendition is mostly to illustrate some of the more prominent aspects of the apparatus 700, such as some of the major components of the computing unit and the spraying unit.

Infection control apparatus 700 is shown to comprise a computing unit further comprising a CPU 721 neatly stored within the cabinet 710, along with a computer monitor 722 and keyboard 723 conveniently placed on shelf 712 outside the cabinet 710, such as for ready access. Any computer mouse in this embodiment is not illustrated, but may be included. The infection control apparatus is also shown to comprise a dispenser 7115, such as for cleaning wipes 711 that can be pulled out as needed. In this way, the bulk of the wipes or other cleaning supplies are hidden inside the cabinet 710. The apparatus also comprises external indicia 770, such as comprising a series of indicator lights. Handle 7145 may be associated with a door on top of the cabinet 710.

With continued reference to FIG. 7, the infection control apparatus comprises three chemical supply tanks, namely tank 746, tank 747 and tank 749. As mentioned, there may be any number of tanks as appropriate for the number of residual self-sanitizing coating compositions included on site. As shown in this embodiment, each tank further comprises both a compressed air supply line and a chemical delivery line. It's important to note this is only a non-limiting example. Tanks may have outlets on the bottom rather than dip tubes from the top for chemical dispensing. Further, in various embodiments, tanks may not require pressurization in order to dispense. In this particular embodiment, the three chemical supply lines 7401 are ganged and connected to a computer controlled switchable valve 7402. The outlet from the valve 7402 provides the inlet 7403 to a fluidic pump 7404. In this way, the computing unit commands the switchable valve 7401 to provide fluidic communication between one or more of the tanks and the inlet 7403 of the fluidic pump 7404. The chosen chemicals from one or more of the tanks may then be pumped to the hose reel 7416 by supply line 7405 and out to the chemical delivery hose 745. The fitting at the end of the chemical delivery hose 745 may then be connected to the appropriate spray gun for delivery the chemicals from the one or more supply tanks.

With further consideration of the embodiment of FIG. 7, the infection control apparatus further comprises an air compressor 7414 that supplies compressed air to the hose reel 7416 via supply line 7415, and also to a computer controlled switchable valve 7412 via the supply line 7413. Commands from the computing unit may then instruct the valve 7412 to send compressed air via one or more of the supply lines 7411 to the appropriate tanks including pressurization. The compressed air sent to the hose reel 7416 may pressurize compressed air supply line 744. The supply line 744 may then be connected to the appropriate inlet of an electrostatic spray gun. In cases where pressurized spraying is performed rather than electrostatic spraying, the compressed air supply line 744 may go unused, even though compressed air may still be directed to one or more of the storage tanks to assist in dispensing. In some embodiments, both compressed air and fluidic pumping are used in concert to move chemical compositions from one or more of the supply tanks out to the chemical delivery hose 745.

As further seen in FIG. 7, this embodiment of an infection control apparatus further comprises a fan 768 that can move heat 769 from inside the cabinet 710 to outside of the cabinet. As mentioned, there may be any number of such fans depending on the ventilation requirements.

Figure 8:
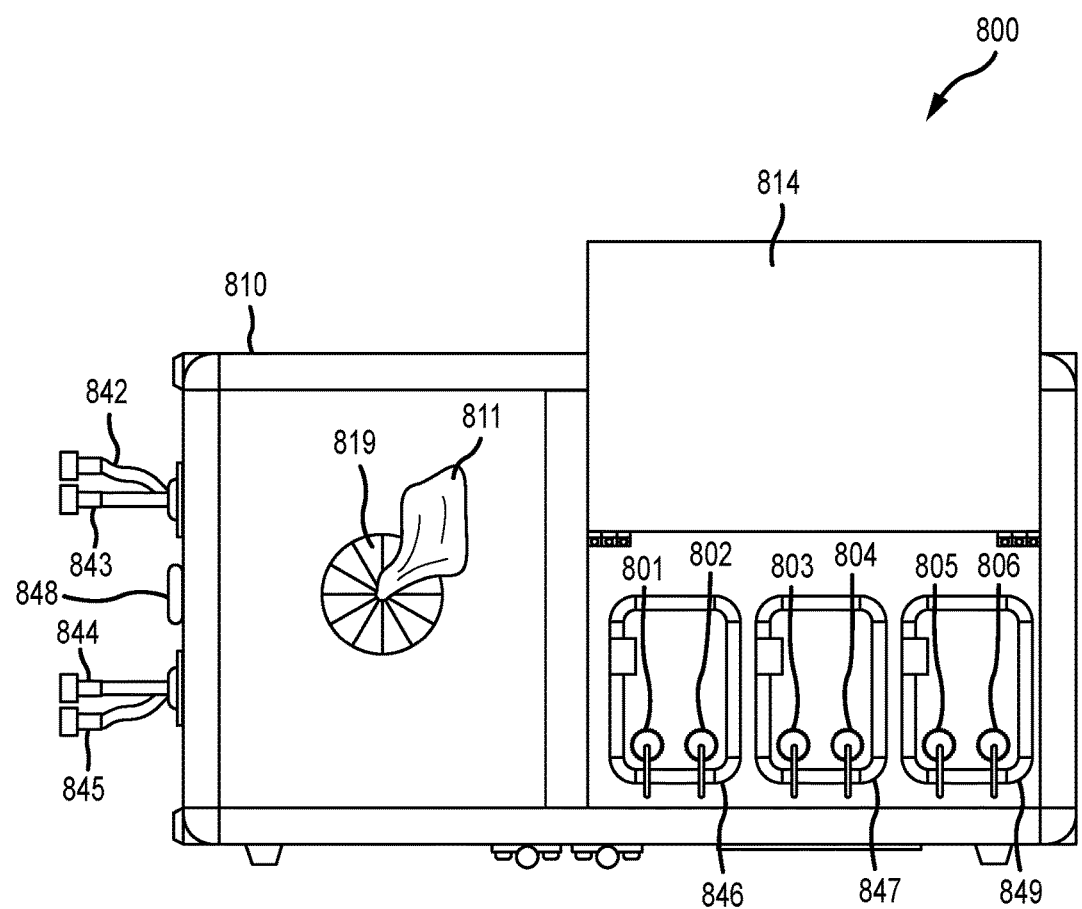
FIG. 8 illustrates a top view of an embodiment of an infection control apparatus with a door in its opened position to reveal components therein, according to various embodiments.

FIG. 8 illustrates a top view of an embodiment of an infection control apparatus 800, with a top door 814 open so as to show the chemical supply tanks residing under the door. As shown, this particular embodiment comprises three tanks, namely tanks 846, 847 and 849, although in various embodiments, an infection control apparatus may comprise any number of chemical supply tanks. In this case, each tank includes both a closure with a dip tube extending into the tank (not entirely visible in the figure) and a compressed air supply line, such as to pressuring the tank to assist dispensing of its contents. Tank 846 further comprises chemical delivery fitting 801 and compressed air supply line and fitting 802. Similarly, tank 847 further comprises chemical delivery fitting 803 and compressed air supply line and fitting 804. Lastly, tank 849 further comprises chemical delivery fitting 805 and compressed air supply line and fitting 806. As mentioned, the chemical delivery fittings may be on the bottom of the chemical supply tanks and thus not visible from a top view.

Operation of the Infection Control Apparatus

In various embodiments, an infection control apparatus as described and exemplified herein is taken into a facility where it is used to mitigate the spread of infections in the facility. As mentioned, the infection control apparatus is configured to (1) identify assets or surfaces on assets suspected to be critical control points in pathogen transfer within a facility, and (2) to spray those surfaces with a residual self-sanitizing coating composition to take those surfaces out of the pathogen transfer process. In various embodiments, an infection control apparatus herein is used to enable an infection control method that includes the steps of tracking assets and their pathogen contamination over time throughout a facility and to enable the step of treating the assets with a residual self-sanitizing coating composition.

A first step in using the infection control apparatus herein is to inventory the assets in a facility and to associate an RFID tag or barcode with each asset as a unique identifier. As mentioned, the user of the apparatus may focus more effort on those assets that are frequently touched or purposely placed into contact with a person, (e.g. bedrails of a hospital bed or an IV stand), and focus less on those assets that are well out of the way of human contact and not likely to harbor pathogens or to be involved in the spread of infections within a facility (e.g. shelves in a storage room). The asset tagging unit of the apparatus, in conjunction with the computing unit, allows for the tagging of assets with a unique identifier such as a barcode or an RFID tag. The user creates a new asset record for each asset of interest in an interactive database on the computer processor (the CPU) of the computing unit. The asset record will initially include the name of the asset. In various embodiments its picture or icon image, its unique identifier (e.g. barcode number or RFID code), and its present location are added to the record, and the asset record may also include information about the types of surfaces on the asset, the surface areas of the touched portions, changing location of the asset (updated e.g. in real time, such as when an audit of RFID tags is automatically performed), and chemical coating information for those assets that have been treated with a residual self-sanitizing coating. Each database record includes fields for each of the necessary information, known initially or to be determined or updated, such as for example, measure of pathogen contamination and residual self-sanitizing coating procedures performed on that asset. Some of the fields are manually filled in, such as by use of the keyboard/mouse of the computing unit whilst others may be automatically filled in, such as with data transmitted electronically. Further to the asset tagging, RF transmitters may be positioned around the facility such that the locations of the assets can be determined in real time without having to find the assets. In various embodiments, the tagging is by way of a barcode, and inventory of the assets may include finding where the asset is, scanning the barcode, and recording the new location of the asset. In various embodiments, rooms or other locations in a facility may be coded, either with a barcode or an RFID tag, such that assets can be associated with particular rooms or other locations in the facility.

A next step in using the infection control apparatus herein is to obtain a measure of the pathogen contamination of each asset. This can be done by swabbing the touched surfaces of an asset using any type of environmental surface sampling and transport swab. Such swabs are usually furnished in a neutralizing buffer and sealed in a vial. The surface under scrutiny is swabbed with the sampling swab, sealed back inside the vial, and then sent to a microbiology laboratory where the sample can be diluted such as through serial dilutions and the latter used to inoculate a number of agar plates. After the agar plates are incubated, the CFU's are counted and a calculation made as the microbial count on the original surface that was swabbed. An exemplary procedure is provided by the CDC, and is entitled "Environmental Hygiene Monitoring—A Guide for Environmental Health Officers," Oct. 5, 2010, Version 3.

Once obtained, a measure of pathogen contamination for the asset is then entered into the record for that particular asset for the day/time swabbed. Measures of pathogen contamination may be obtained and entered into the database in units of $\log_{10}$ CFU's/cm$^2$, or other suitable units representing number of organisms per unit of surface area. Contamination when found, and depending on the facility and type of microorganism, may be on the order of from about 1 $\log_{10}$ CFU's/cm$^2$ to about 10 $\log_{10}$ CFU's/cm$^2$.

The measure of pathogen contamination initially found on an asset can be recorded as the measure of pathogen contamination at $t_0$. In various embodiments, this information can be manually entered into the appropriate field in the asset record. Environmental surface test swabs may be sent over to the microbiology laboratory present in the very same medical center where the infection control is being implemented. Further information may be added to the asset record, including the identity of the species of microorganisms found on the asset, such as gleaned from the appearance of the agar plate colonies used for the CFU counts or as confirmed by genetic testing.

An optional step in the method of infection control in accordance to various embodiments of the present disclosure comprises DNA or RNA sequencing of the pathogens found on an asset. In conjunction with the previous step, if a pathogen is found on an asset, particularly a pathogen known to cause an HAI, then DNA/RNA sequencing may be performed to obtain genetic information regarding the pathogen. DNA/RNA sequencing may be performed onsite such as by employing a portable DNA/RNA sequencing unit, or samples may be sent off site. The measure of pathogen contamination and the genetic sequencing may be performed by the same laboratory. The genetic information may then be entered into the database for the particular asset associated with the contamination.

Another step in using the infection control apparatus herein is to periodically inventory where the assets are and to repeat the surface swabbing with surface testing swabs to obtain updated measures of pathogen contamination. In various embodiments, the inventory is triggered from the computer processor, wherein the RFID tags are accounted for all at the same time, by way of remote RF transmitters placed around the facility. A schedule can be created and modified as necessary, including the periodicity for inventory of the assets and swabbing of the surfaces for measures of pathogen contamination. This process is repeated over time as the assets move around the facility. The time period over which data is collected prior to an assessment as to which assets are the critical control points varies. The overall time period for the assessment may be a day or a few days, or a week or a few weeks, or months, or even longer. An analysis of the existing data sets may be performed at any time, and there may be a plurality of data sets obtained over a period of time comprising the infection control study.

Asset location and measure of pathogen contamination for each of the assets may be performed after the passage of predetermined time periods, such as in accordance to a particular schedule of time periods, beginning with initial location and measure of pathogen contamination at $t_0$, and then again at $t_1$, $t_2$, $t_3$, etc. These time periods may be of any length, such as minutes, hours, days or weeks, and are not necessarily the same (i.e., $t_2-t_1$ does not need to equal $t_1-t_0$, and so forth). In various embodiments, data sets comprising location of assets and present measures of pathogen contamination may be obtained on a daily basis (i.e. every 24-hours, such as on a precise schedule). Thus, after 5-days there will be 5 data sets for analysis. At any time period, DNA or RNA sequencing information may be obtained and added to the asset records for particular assets.

For convenience, the initial data points, including asset location, measure of pathogen contamination, and optionally, genetic sequencing, may be referred to, for example, as the "first set of data" or "Data Set 1." Then the data obtained after the passage of a prescribed period of time, such as 24-hours, i.e. at $t_1$, may be referred to, for example, as the "second set of data" or "Data Set 2." Repeating the asset inventory and the measure of pathogen contamination for each asset at multiple time periods, $t_2$, $t_3$, $t_4$, $t_5$, etc., such as every 24 hours, results in the collection of multiple data sets for analysis by the computer processor. Each of these data sets is entered into the computer processor. Some of the data, such as RFID locations, may be electronically transferred to the computer processor, whereas measures of pathogen contamination and optional genetic sequencing may be manually entered into the computer processor.

A next step in using the infection control apparatus herein is to engage the computing system to identify the critical control points in the facility, given the data that has been acquired and entered into the computer processor and based on a set of criteria. The analysis may involve as few as two sets of data, that is, initial asset locations and initial measures of pathogen contamination at $t_0$ and a second set of locations and pathogen contamination measurements at $t_1$, or may involve more than two data sets. The database including the location of assets over time, the measures of pathogen contamination on the assets over time, along with the optional DNA/RNA sequencing data and species identification, are used by an algorithm of the computer processor to obtain the identity of assets that are the transfer points for pathogens and are thus the crossroads in the spread of infection in the facility.

The criteria for the computer implemented determination of what constitutes a critical control point may vary as needed, based on such factors as the nature of the facility (e.g. healthcare versus foodservice), the history of illnesses seen at the facility, and other considerations. The software may be reprogrammed to change criteria the algorithm uses to categorize assets as critical control points. In some embodiments, an asset, regardless of its movement or stationary status in the facility, may be deemed a critical control point if it has a measurable pathogen contamination on two consecutive data collection times, such as at $t_0$ and $t_1$, indicating the asset wasn't cleaned properly, may never be cleaned properly, and could perhaps be involved in pathogen transfer and spread of infection in the future. Thus, such an asset having fit the criteria for assignment as a critical control point can be identified as such in a report provided by the computer processor. The asset may then be destined for coating with a residual self-sanitizing composition such that it can no longer sustain viable pathogens.

In other embodiments, the criteria whether an asset is a critical control point may be whether the asset moved and a measurable pathogen contamination appeared on a previously clean asset in the new location of the moved asset. In this scenario, the asset moved with a pathogen contamination and then someone likely touched the contaminated asset and transferred pathogens to the other asset. Thus, the asset that moved may be deemed a critical control point, having been determined by the algorithm to fit the criteria. The asset may then be destined for coating with a residual self-sanitizing composition such that it can no longer sustain viable pathogens. Genetic testing aids the computer implemented decision making as to what constitutes a critical control point, because an organism that appears new within the facility and determined to not be generationally related to another pathogen also found in the facility, wasn't likely transferred by the asset found contaminated, and likely came into the facility via an infected person. Thus the asset it was found on may not be deemed a critical control point. Further, at the next data collection time, the asset may be found to no longer harbor this pathogen, meaning the asset was properly cleaned and not a critical control point.

Another step in using the infection control apparatus herein is to spray the assets identified as critical control points with one or more residual self-sanitizing coating compositions as described herein. As indicated, as an asset is sprayed, the spraying unit of the infection control apparatus records the duration of spraying and either the rate of spray or the decrease in the weight of a tank of chemicals, such that the operator knows how much composition is applied to a surface. Further, environmental conditions such as temperature and relative humidity may be recorded at the same time, since these and other conditions may affect the dry times for the compositions. At this time, the operator may enter into the database the surface area of the asset surface being treated and which compositions are applied. The infection control apparatus keeps track of the other variables, such as the spray time and amount of materials sprayed. As mentioned, the type of spray may be any type of spraying appropriate for the surface, such as electrostatic spray. For neutral, non-metallic surfaces, other spray methods may be employed, with the appropriate spray gun attached to the chemical delivery hose of the spray module.

After the suspected critical control surfaces are coated with the appropriate residual self-sanitizing coating, the tracking of assets and the swabbing for pathogens can continue, and the assessment following another time period will be indicative of the veracity of the procedure. For example, it may be found that previously heavily contaminated and trafficked surfaces of assets no longer harbor pathogens, and that pathogens are no longer transferred along their previous routes. Depending on the chemistry involved, the coated surfaces may be tested for efficacy of the coating and/or the presence of coating, and recoated as necessary. The computing unit of the infection control apparatus is again engaged in recording the coating schedule of particular assets. In various embodiments, a facility will track the incidence of HAI over certain periods of time (e.g. quarterly or annually) and a reduction in HAI is an indication that the infection control method as performed by the present infection control apparatus is working as designed.

An infection control apparatus and method for using the apparatus for control of pathogen spread in a facility are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

As used herein, "satisfy", "meet", "match", "associated with" or similar phrases may include an identical match, a partial match, meeting certain criteria, matching a subset of data, a correlation, satisfying certain criteria, a correspondence, an association, an algorithmic relationship and/or the like.

Terms and phrases similar to "associate" and/or "associating" may include tagging, flagging, correlating, using a look-up table or any other method or system for indicating or creating a relationship between elements, such as, for example, (i) an account and (ii) a healthcare asset and/or digital channel. Moreover, the associating may occur at any point, in response to any suitable action, event, or period of time. The associating may occur at pre-determined intervals, periodic, randomly, once, more than once, or in response to a suitable request or action. Any of the information may be distributed and/or accessed via a software enabled link, wherein the link may be sent via an email, text, post, social network input and/or any other method known in the art.

The system or any components may integrate with system integration technology such as, for example, the ALEXA system developed by AMAZON. Alexa is a cloud-based voice service that can help you with tasks, entertainment, general information and more. All Amazon Alexa devices, such as the Amazon Echo, Amazon Dot, Amazon Tap and Amazon Fire TV, have access to the Alexa Voice Service. The system may receive voice commands via its voice activation technology, and activate other functions, control smart devices and/or gather information. For example, music, emails, texts, calling, questions answered, home improvement information, smart home communication/activation, games, shopping, making to-do lists, setting alarms, streaming podcasts, playing audiobooks, and providing weather, traffic, and other real time information, such as news. The system may allow the user to access information about eligible accounts linked to an online account across all Alexa-enabled devices.

As used herein, big data may refer to partially or fully structured, semi-structured, or unstructured data sets including millions of rows and hundreds of thousands of columns. Big data sets may be compiled without descriptive metadata such as column types, counts, percentiles, or other interpretive-aid data points.

Distributed computing cluster may be, for example, a Hadoop® cluster configured to process and store big data sets with some of nodes comprising a distributed storage system and some of nodes comprising a distributed processing system. In that regard, distributed computing cluster may be configured to support a Hadoop® distributed file system (HDFS) as specified by the Apache Software Foundation at http://hadoop.apache.org/docs/. For more information on big data management systems, see U.S. Ser. No. 14/944,902 titled INTEGRATED BIG DATA INTERFACE FOR MULTIPLE STORAGE TYPES and filed on Nov. 18, 2015; U.S. Ser. No. 14/944,979 titled SYSTEM AND METHOD FOR READING AND WRITING TO BIG DATA STORAGE FORMATS and filed on Nov. 18, 2015; U.S. Ser. No. 14/945,032 titled SYSTEM AND METHOD FOR CREATING, TRACKING, AND MAINTAINING BIG DATA USE CASES and filed on Nov. 18, 2015; U.S. Ser. No. 14/944,849 titled SYSTEM AND METHOD FOR AUTOMATICALLY CAPTURING AND RECORDING LINEAGE DATA FOR BIG DATA RECORDS and filed on Nov. 18, 2015; U.S. Ser. No. 14/944,898 titled SYSTEMS AND METHODS FOR TRACKING SENSITIVE DATA IN A BIG DATA ENVIRONMENT and filed on Nov. 18, 2015; and U.S. Ser. No. 14/944,961 titled SYSTEM AND METHOD TRANSFORMING SOURCE DATA INTO OUTPUT DATA IN BIG DATA ENVIRONMENTS and filed on Nov. 18, 2015, the contents of each of which are herein incorporated by reference in their entirety.

Any communication, transmission and/or channel discussed herein may include any system or method for delivering content (e.g. data, information, metadata, etc), and/or the content itself. The content may be presented in any form or medium, and in various embodiments, the content may be delivered electronically and/or capable of being presented electronically. For example, a channel may comprise a website or device (e.g., Facebook, YOUTUBE®, APPLE®TV®, PANDORA®, XBOX®, SONY® PLAYSTATION®), a uniform resource locator ("URL"), a document (e.g., a MICROSOFT® Word® document, a MICROSOFT® Excel® document, an ADOBE® .pdf document, etc.), an "ebook," an "emagazine," an application or microapplication (as described herein), an SMS or other type of text message, an email, facebook, twitter, MMS and/or other type of communication technology. In various embodiments, a channel may be hosted or provided by a data partner. In various embodiments, the distribution channel may comprise at least one of a merchant website, a social media website, affiliate or partner websites, an external vendor, a mobile device communication, social media network and/or location based service. Distribution channels may include at least one of a merchant website, a social media site, affiliate or partner websites, an external vendor, and a mobile device communication. Examples of social media sites include FACEBOOK®, FOURSQUARE®, TWITTER®, MYSPACE®, LINKEDIN®, and the like. Examples of affiliate or partner websites include AMERICAN EXPRESS®, GROUPON®, LIVINGSOCIAL®, and the like. Moreover, examples of mobile device communications include texting, email, and mobile applications for smartphones.

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; patient data; hospital data; germ data and/or like data useful in the operation of the system. As those skilled in the art will appreciate, user computer may include an operating system (e.g., WINDOWS®, OS2, UNIX®, LINUX®, SOLARIS®, MacOS, etc.) as well as various conventional support software and drivers typically associated with computers.

The present system or any part(s) or function(s) thereof may be implemented using hardware, software or a combination thereof and may be implemented in one or more computer systems or other processing systems. However, the manipulations performed by embodiments were often referred to in terms, such as matching or selecting, which are commonly associated with mental operations performed by a human operator. No such capability of a human operator is necessary, or desirable in most cases, in any of the operations described herein. Rather, the operations may be machine operations. Useful machines for performing the various embodiments include general purpose digital computers or similar devices.

In fact, in various embodiments, the embodiments are directed toward one or more computer systems capable of carrying out the functionality described herein. The computer system includes one or more processors, such as processor. The processor is connected to a communication infrastructure (e.g., a communications bus, cross-over bar, or network). Various software embodiments are described in terms of this exemplary computer system. After reading this description, it will become apparent to a person skilled in the relevant art(s) how to implement various embodiments using other computer systems and/or architectures. Computer system can include a display interface that forwards graphics, text, and other data from the communication infrastructure (or from a frame buffer not shown) for display on a display unit.

Computer system also includes a main memory, such as for example random access memory (RAM), and may also include a secondary memory. The secondary memory may include, for example, a hard disk drive and/or a removable storage drive, representing a floppy disk drive, a magnetic tape drive, an optical disk drive, etc. The removable storage drive reads from and/or writes to a removable storage unit in a well-known manner. Removable storage unit represents a floppy disk, magnetic tape, optical disk, etc. which is read by and written to by removable storage drive. As will be appreciated, the removable storage unit includes a computer usable storage medium having stored therein computer software and/or data.

In various embodiments, secondary memory may include other similar devices for allowing computer programs or other instructions to be loaded into computer system. Such devices may include, for example, a removable storage unit and an interface. Examples of such may include a program cartridge and cartridge interface (such as that found in video game devices), a removable memory chip (such as an erasable programmable read only memory (EPROM), or programmable read only memory (PROM)) and associated socket, and other removable storage units and interfaces, which allow software and data to be transferred from the removable storage unit to computer system.

Computer system may also include a communications interface. Communications interface allows software and data to be transferred between computer system and external devices. Examples of communications interface may include a modem, a network interface (such as an Ethernet card), a communications port, a Personal Computer Memory Card International Association (PCMCIA) slot and card, etc. Software and data transferred via communications interface are in the form of signals which may be electronic, electromagnetic, optical or other signals capable of being received by communications interface. These signals are provided to communications interface via a communications path (e.g., channel). This channel carries signals and may be implemented using wire, cable, fiber optics, a telephone line, a cellular link, a radio frequency (RF) link, wireless and other communications channels.

The terms "computer program medium" and "computer usable medium" and "computer readable medium" are used to generally refer to media such as removable storage drive and a hard disk installed in hard disk drive. These computer program products provide software to computer system.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

In various embodiments, software may be stored in a computer program product and loaded into computer system using removable storage drive, hard disk drive or communications interface. The control logic (software), when executed by the processor, causes the processor to perform the functions of various embodiments as described herein. In various embodiments, hardware components such as application specific integrated circuits (ASICs). Implementation of the hardware state machine so as to perform the functions described herein will be apparent to persons skilled in the relevant art(s).

In various embodiments, the server may include application servers (e.g. WEB SPHERE, WEB LOGIC, JBOSS, EDB® Postgres Plus Advanced Server® (PPAS), etc.). In various embodiments, the server may include web servers (e.g. APACHE, IIS, GWS, SUN JAVA® SYSTEM WEB SERVER, JAVA Virtual Machine running on LINUX or WINDOWS).

A web client includes any device (e.g., personal computer) which communicates via any network, for example such as those discussed herein. Such browser applications comprise Internet browsing software installed within a computing unit or a system to conduct other communications or germ mapping. These computing units or systems may take the form of a computer or set of computers, although other types of computing units or systems may be used, including laptops, notebooks, tablets, hand held computers, personal digital assistants, set-top boxes, workstations, computer-servers, main frame computers, mini-computers, PC servers, pervasive computers, network sets of computers, personal computers, such as IPADS®, IMACS®, and MAC-BOOKS®, kiosks, terminals, point of sale (POS) devices and/or terminals, televisions, or any other device capable of receiving data over a network. A web-client may run MICROSOFT® INTERNET EXPLORER®, MOZILLA® FIREFOX®, GOOGLE® CHROME®, APPLE® Safari, or any other of the myriad software packages available for browsing the internet.

Practitioners will appreciate that a web client may or may not be in direct contact with an application server. For example, a web client may access the services of an application server through another server and/or hardware component, which may have a direct or indirect connection to an Internet server. For example, a web client may communicate with an application server via a load balancer. In various embodiments, access is through a network or the Internet through a commercially-available web-browser software package.

As those skilled in the art will appreciate, a web client includes an operating system (e.g., WINDOWS®/CE/Mobile, OS2, UNIX®, LINUX®, SOLARIS®, MacOS, etc.) as well as various conventional support software and drivers typically associated with computers. A web client may include any suitable personal computer, network computer, workstation, personal digital assistant, cellular phone, smart phone, minicomputer, mainframe or the like. A web client can be in a home or business environment with access to a network. In various embodiments, access is through a network or the Internet through a commercially available web-browser software package. A web client may implement security protocols such as Secure Sockets Layer (SSL) and Transport Layer Security (TLS). A web client may implement several application layer protocols including http, https, ftp, and sftp.

In various embodiments, components, modules, and/or engines of a system may be implemented as micro-applications or micro-apps. Micro-apps are typically deployed in the context of a mobile operating system, including for example, a WINDOWS® mobile operating system, an ANDROID® Operating System, APPLE® IOS®, a BLACKBERRY® operating system and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

As used herein, the term "network" includes any cloud, cloud computing system or electronic communications system or method which incorporates hardware and/or software components. Communication among the parties may be accomplished through any suitable communication channels, such as, for example, a telephone network, an extranet, an intranet, Internet, point of interaction device (point of sale device, personal digital assistant (e.g., IPHONE®, BLACKBERRY®), cellular phone, kiosk, etc.), online communications, satellite communications, off-line communications, wireless communications, transponder communications, local area network (LAN), wide area network (WAN), virtual private network (VPN), networked or linked devices, keyboard, mouse and/or any suitable communication or data input modality. Moreover, although the system is frequently described herein as being implemented with TCP/IP communications protocols, the system may also be implemented using IPX, APPLE®talk, IP-6, NetBIOS®, OSI, any tunneling protocol (e.g. IPsec, SSH), or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, DILIP NAIK, INTERNET STANDARDS AND PROTOCOLS (1998); JAVA® 2 COMPLETE, various authors, (Sybex 1999); DEBORAH RAY AND ERIC RAY, MASTERING HTML 4.0 (1997); and LOSHIN, TCP/IP CLEARLY EXPLAINED (1997) and DAVID GOURLEY AND BRIAN TOTTY, HTTP, THE DEFINITIVE GUIDE (2002), the contents of which are hereby incorporated by reference.

The various system components may be independently, separately or collectively suitably coupled to the network via data links which includes, for example, a connection to an Internet Service Provider (ISP) over the local loop as is typically used in connection with standard modem communication, cable modem, Dish Networks®, ISDN, Digital Subscriber Line (DSL), or various wireless communication methods, see, e.g., GILBERT HELD, UNDERSTANDING DATA COM- MUNICATIONS (1996), which is hereby incorporated by reference. It is noted that the network may be implemented as other types of networks, such as an interactive television (ITV) network. Moreover, the system contemplates the use, sale or distribution of any goods, services or information over any network having similar functionality described herein.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand. For more information regarding cloud computing, see the NIST's (National Institute of Standards and Technology) definition of cloud computing at http://csrc.nist.gov/publications/nistpubs/800-145/SP800-145.pdf (last visited June 2012), which is hereby incorporated by reference in its entirety.

The system contemplates uses in association with web services, utility computing, pervasive and individualized computing, security and identity solutions, autonomic computing, cloud computing, commodity computing, mobility and wireless solutions, open source, biometrics, grid computing and/or mesh computing.

Any databases discussed herein may include relational, hierarchical, graphical, blockchain, object-oriented structure and/or any other database configurations. Common database products that may be used to implement the databases include DB2 by IBM® (Armonk, N.Y.), various database products available from ORACLE® Corporation (Redwood Shores, Calif.), MICROSOFT® Access® or MICROSOFT® SQL Server® by MICROSOFT® Corporation (Redmond, Wash.), MySQL by MySQL AB (Uppsala, Sweden), MongoDB®, Redis®, Apache Cassandra®, or any other suitable database product. Moreover, the databases may be organized in any suitable manner, for example, as data tables or lookup tables. Each record may be a single file, a series of files, a linked series of data fields or any other data structure.

The blockchain structure may include a distributed database that maintains a growing list of data records. The blockchain may provide enhanced security because each block may hold individual data elements and the results of any blockchain executables. Each block may contain a timestamp and a link to a previous block. Blocks may be linked because each block may include the hash of the prior block in the blockchain. The linked blocks form a chain, with only one successor block allowed to link to one other predecessor block.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); Binary Large Object (BLOB); stored as ungrouped data elements encoded using ISO/IEC 7816-6 data elements; stored as ungrouped data elements encoded using ISO/IEC Abstract Syntax Notation (ASN.1) as in ISO/IEC 8824 and 8825; and/or other proprietary techniques that may include fractal compression methods, image compression methods, etc.

In various embodiments, the ability to store a wide variety of information in different formats is facilitated by storing the information as a BLOB. Thus, any binary information can be stored in a storage space associated with a data set. As discussed above, the binary information may be stored in association with the system or external to but affiliated with system. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data, in the database or associated with the system, by multiple and unrelated owners of the data sets. For example, a first data set which may be stored may be provided by a first party, a second data set which may be stored may be provided by an unrelated second party, and yet a third data set which may be stored, may be provided by an third party unrelated to the first and second party. Each of these three exemplary data sets may contain different information that is stored using different data storage formats and/or techniques. Further, each data set may contain subsets of data that also may be distinct from other subsets.

As stated above, in various embodiments, the data can be stored without regard to a common format. However, the data set (e.g., BLOB) may be annotated in a standard manner when provided for manipulating the data in the database or system. The annotation may comprise a short header, trailer, or other appropriate indicator related to each data set that is configured to convey information useful in managing the various data sets. For example, the annotation may be called a "condition header", "header", "trailer", or "status", herein, and may comprise an indication of the status of the data set or may include an identifier correlated to a specific issuer or owner of the data. In one example, the first three bytes of each data set BLOB may be configured or configurable to indicate the status of that particular data set; e.g., LOADED, INITIALIZED, READY, BLOCKED, REMOVABLE, or DELETED. Subsequent bytes of data may be used to indicate for example, the identity of the user, healthcare entity, patient account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the various entities involved. Furthermore, the security information may restrict/permit only certain actions such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate.

The data, including the header or trailer may be received by a standalone interaction device configured to add, delete, modify, or augment the data in accordance with the header or trailer. As such, in one embodiment, the header or trailer is not stored on a device along with the associated data, but instead the appropriate action may be taken by providing to the user at the standalone device, the appropriate option for the action to be taken. The system may contemplate a data storage arrangement wherein the header or trailer, or header or trailer history, of the data is stored on the system, device or app in relation to the appropriate data.

One skilled in the art will also appreciate that, for security reasons, any databases, systems, devices, servers or other components of the system may consist of any combination thereof at a single location or at multiple locations, wherein each database or system includes any of various suitable security features, such as firewalls, access codes, encryption, decryption, compression, decompression, and/or the like.

Encryption may be performed by way of any of the techniques now available in the art or which may become available—e.g., Twofish, RSA, El Gamal, Schorr signature, DSA, PGP, PKI, GPG (GnuPG), and symmetric and asymmetric cryptosystems.

The computing unit of the web client may be further equipped with an Internet browser connected to the Internet or an intranet using standard dial-up, cable, DSL or any other Internet protocol known in the art. Data or operations originating at a web client may pass through a firewall in order to prevent unauthorized access from users of other networks. Further, additional firewalls may be deployed between the varying components of CMS to further enhance security.

Firewall may include any hardware and/or software suitably configured to protect CMS components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based, access control lists, and Packet Filtering among others. Firewall may be integrated within a web server or any other CMS components or may further reside as a separate entity. A firewall may implement network address translation ("NAT") and/or network address port translation ("NAPT"). A firewall may accommodate various tunneling protocols to facilitate secure communications, such as those used in virtual private networking. A firewall may implement a demilitarized zone ("DMZ") to facilitate communications with a public network such as the Internet. A firewall may be integrated as software within an Internet server, any other application server components or may reside within another computing device or may take the form of a standalone hardware component.

The computers discussed herein may provide a suitable website or other Internet-based graphical user interface which is accessible by users. In one embodiment, the MICROSOFT® INTERNET INFORMATION SERVICES® (IIS), MICROSOFT® Transaction Server (MTS), and MICROSOFT® SQL Server, are used in conjunction with the MICROSOFT® operating system, MICROSOFT® NT web server software, a MICROSOFT® SQL Server database system, and a MICROSOFT® Commerce Server. Additionally, components such as Access or MICROSOFT® SQL Server, ORACLE®, Sybase, Informix MySQL, Interbase, etc., may be used to provide an Active Data Object (ADO) compliant database management system. In one embodiment, the Apache web server is used in conjunction with a Linux operating system, a MySQL database, and the Perl, PHP, Ruby, and/or Python programming languages.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® applets, JAVASCRIPT, active server pages (ASP), common gateway interface scripts (CGI), extensible markup language (XML), dynamic HTML, cascading style sheets (CSS), AJAX (Asynchronous JAVASCRIPT And XML), helper applications, plug-ins, and the like. A server may include a web service that receives a request from a web server, the request including a URL and an IP address (123.56.789.234). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. See, e.g., ALEX NGHIEM, IT WEB SERVICES: A ROADMAP FOR THE ENTERPRISE (2003), hereby incorporated by reference. For example, representational state transfer (REST), or RESTful, web services may provide one way of enabling interoperability between applications.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on the Internet server. Middleware may be configured to process transactions between the various components of an application server and any number of internal or external systems for any of the purposes disclosed herein. WEBSPHERE MQ™ (formerly MQSeries) by IBM®, Inc. (Armonk, N.Y.) is an example of a commercially available middleware product. An Enterprise Service Bus ("ESB") application is another example of middleware.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The system and method may be described herein in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, JAVA®, JAVASCRIPT, JAVASCRIPT Object Notation (JSON), VBScript, Macromedia Cold Fusion, COBOL, MICROSOFT® Active Server Pages, assembly, PERL, PHP, awk, Python, Visual Basic, SQL Stored Procedures, PL/SQL, any UNIX shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "JAVA® Cryptography" by Jonathan Knudson, published by O'Reilly & Associates (1998); (3) "Cryptography & Network Security: Principles & Practice" by William Stallings, published by Prentice Hall; all of which are hereby incorporated by reference.

In various embodiments, the software elements of the system may also be implemented using Node.js®. Node.js® may implement several modules to handle various core functionalities. For example, a package management module, such as Npm®, may be implemented as an open source library to aid in organizing the installation and management of third-party Node.js® programs. Node.js® may also implement a process manager, such as, for example, Parallel Multithreaded Machine ("PM2"); a resource and performance monitoring tool, such as, for example, Node Application Metrics ("appmetrics"); a library module for building user interfaces, such as for example ReachJS®; and/or any other suitable and/or desired module.

As will be appreciated by one of ordinary skill in the art, the system may be embodied as a customization of an existing system, an add-on product, a processing apparatus executing upgraded software, a stand alone system, a distributed system, a method, a data processing system, a device for data processing, and/or a computer program product. Accordingly, any portion of the system or a module may take the form of a processing apparatus executing code, an internet based embodiment, an entirely hardware embodiment, or an embodiment combining aspects of the internet, software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The system and method is described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user WINDOWS®, webpages, websites, web forms, prompts, etc. Practitioners will appreciate that the illustrated steps described herein may comprise in any number of configurations including the use of WINDOWS®, webpages, web forms, popup WINDOWS®, prompts and the like. It should be further appreciated that the multiple steps as illustrated and described may be combined into single webpages and/or WINDOWS® but have been expanded for the sake of simplicity. In other cases, steps illustrated and described as single process steps may be separated into multiple webpages and/or WINDOWS® but have been combined for simplicity.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for an apparatus or component of an apparatus, or method in using an apparatus to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

We claim:

1. An infection control apparatus comprising:
   an asset tagging unit;
   a spraying unit;
   a power supply unit;
   a DNA/RNA sequencing unit; and
   a computing unit comprising a non-transitory computer-readable medium encoded with program instructions for controlling the asset tagging unit, the spraying unit and the DNA/RNA sequencing unit, to perform a method of infection control in a facility.

2. The infection control apparatus of claim 1, wherein the program instructions control the power supply unit.

3. The infection control apparatus of claim 1, further comprising a cabinet physically enclosing at least a portion of the apparatus.

4. The infection control apparatus of claim 3, wherein the cabinet further comprises a set of wheels to mobilize the infection control apparatus as a cart.

5. The infection control apparatus of claim 3, further comprising external indicia positioned outside of the cabinet and controlled by the program instructions, the external indicia further comprising an LED screen or indicator lights.

6. The infection control apparatus of claim 3, wherein the cabinet further comprises at least one hinged door.

7. The infection control apparatus of claim 1, wherein the computing unit comprises a desktop computer, a laptop computer, or a tablet.

8. The infection control apparatus of claim 1, wherein the asset tagging unit further comprises an RFID reader and a plurality of RFID tags, each tag readable by the RFID reader and each tag associated with an asset located inside the facility, and wherein the program instructions further comprise RFID asset management software that provides instruction to the RFID reader.

9. The infection control apparatus of claim 8, further comprising a plurality of RFID readers stationed around the inside of the facility capable of obtaining and transmitting the location of each one of the plurality of RFID tags to the non-transitory computer-readable medium upon command from the RFID asset management software.

10. An infection control apparatus comprising:
    an asset tagging unit;
    a spraying unit;
    a power supply unit; and
    a computing unit comprising a non-transitory computer-readable medium encoded with program instructions for controlling the asset tagging unit and the spraying unit to perform a method of infection control in a facility,
    wherein the asset tagging unit comprises a barcode printer, a barcode reader, and a plurality of barcode labels printed by the barcode printer, each label readable by the barcode reader and each label associated with an asset located inside the facility.

11. The infection control apparatus of claim 10, wherein the spraying unit further comprises a tank module and a spray module.

12. The infection control apparatus of claim 11, wherein the tank module further comprises at least two tanks, each tank further comprises at least one of a weight sensor, a liquid level float, and an optical sensor controlled by the program instructions.

13. The infection control apparatus of claim 12, wherein the spray module comprises (i) at least one spray gun; (ii) an air compressor and at least two compressed air supply lines, each compressed air supply line connecting the air compressor and each of the at least two tanks in fluidic communication to pressurize each tank; and (iii) at least two chemical supply lines, each chemical supply line connecting one of the at least two tanks and the at least one spray gun in fluidic communication.

14. The infection control apparatus of claim 13, wherein each of the compressed air supply lines and the chemical supply lines are managed on retractable hose reels.

15. The infection control apparatus of claim 12, wherein the spray module comprises a fluidic pump having an inlet and an outlet, a spray gun, a chemical supply line, and a switchable valve controlled by the program instructions, wherein the at least two tanks are in fluidic communication with the switchable valve, the switchable valve is in fluidic communication with the inlet of the fluidic pump, and the chemical supply line provides fluidic communication between the outlet of the fluidic pump and the spray gun.

16. The infection control apparatus of claim 15, wherein the chemical supply line is on a retractable hose reel.

17. A method of infection control in a facility containing a plurality of assets capable of changing locations within the facility, the method comprising:
providing the infection control apparatus of claim 1;
creating a unique asset record for each asset;
associating each asset record with a unique asset identifier comprising either a printed barcode label or an RFID tag;
physically tagging each asset with its associated asset identifier by attaching the barcode label or the RFID tag to the asset;
swabbing a surface of each asset with a surface testing swab to obtain a measure of pathogen contamination on the surface of the asset;
obtaining the location of each asset;
inputting the location of each asset and the measure of pathogen contamination on the surface of the asset to the computing unit as a first set of data;
repeating the swabbing and obtaining steps for each asset after a period of time, and inputting the location of each asset and the measure of pathogen contamination on the surface of the asset to the computing unit as a second set of data;
analyzing the data sets to determine which assets meet predetermined criteria to be categorized as critical control points within the facility; and
spraying each asset categorized as a critical control point with a residual self-sanitizing coating composition delivered from the spraying unit.

18. The method of claim 17, wherein the data sets further comprise DNA/RNA sequencing of the pathogen contamination on the surface of the asset.

19. The method of claim 17, wherein obtaining the location of each asset comprises instructing a plurality of RFID readers stationed around the inside of the facility to obtain the location of each RFID tag and to transmit the asset locations to the non-transitory computer-readable medium.

* * * * *